(12) United States Patent
Cook

(10) Patent No.: US 6,546,378 B1
(45) Date of Patent: Apr. 8, 2003

(54) SIGNAL INTERPRETATION ENGINE

(75) Inventor: Daniel Reed Cook, Bountiful, UT (US)

(73) Assignee: Bright Ideas, L.L.C., Bountiful, UT (US)

( * ) Notice: Subject to any disclaimer, the term of this patent is extended or adjusted under 35 U.S.C. 154(b) by 0 days.

(21) Appl. No.: 08/840,052

(22) Filed: Apr. 24, 1997

(51) Int. Cl.[7] .............................................. G06F 15/18
(52) U.S. Cl. ............................ 706/12; 706/20; 382/159
(58) Field of Search ................................ 706/52, 2, 20, 706/12; 382/159

(56) References Cited

U.S. PATENT DOCUMENTS

| | | | | |
|---|---|---|---|---|
| 4,883,067 A | | 11/1989 | Knispel et al. ............. 600/545 |
| 5,222,210 A | * | 6/1993 | Leivian ........................ 706/40 |
| 5,253,332 A | * | 10/1993 | Kumamoto ................... 706/52 |
| 5,255,347 A | * | 10/1993 | Matsuba et al. .............. 706/20 |
| 5,353,380 A | * | 10/1994 | Zhang .......................... 706/52 |
| 5,355,435 A | | 10/1994 | DeYong et al. ............... 706/26 |
| 5,377,100 A | | 12/1994 | Pope et al. ................... 600/545 |
| 5,379,268 A | | 1/1995 | Hutson ........................ 367/100 |
| 5,402,521 A | * | 3/1995 | Niida et al. ................... 706/21 |
| 5,434,955 A | * | 7/1995 | Kumamoto ................... 706/52 |
| 5,465,321 A | | 11/1995 | Smyth .......................... 706/20 |
| 5,470,081 A | | 11/1995 | Sato et al. ............... 273/148 B |
| 5,474,082 A | | 12/1995 | Junker ......................... 128/905 |
| 5,485,551 A | * | 1/1996 | Ejima et al. .................. 706/52 |
| 5,515,477 A | | 5/1996 | Sutherland ................... 706/41 |
| 5,524,176 A | * | 6/1996 | Narita et al. .................. 706/52 |
| 5,571,057 A | | 11/1996 | Ayers .......................... 463/36 |
| 5,579,439 A | * | 11/1996 | Khan ............................ 706/2 |
| 5,583,771 A | * | 12/1996 | Lynch et al. .................. 706/20 |
| 5,617,513 A | * | 4/1997 | Schnitta ....................... 706/21 |
| 5,651,100 A | * | 7/1997 | Hayashi et al. ............... 706/52 |
| 5,687,286 A | * | 11/1997 | Bar-Yam ...................... 706/20 |

OTHER PUBLICATIONS

J.J. Rajan and P.J.W. Rayner, "Time Series Classification using the Volterra Connectionist Model and Bayes Decision Theory," IEEE Int'l. Conf. on Acoustics, Speech and Signal Processing, vol. 1, pp. 601–604, Apr. 1993.*
NeuralWare Brochure, "NeuralWorks Professional II/PLUSv5.0," 2 pages, Dec. 1993.*
J.J. Rajan and P.J.W. Rayner, "Unsupervised time series classification," Signal Processing, vol. 46(1), pp. 57–74, Sep. 1995.*

* cited by examiner

Primary Examiner—Robert W. Downs
(74) Attorney, Agent, or Firm—Pate Pierce & Baird

(57) ABSTRACT

A signal interpretation engine apparatus and method are disclosed in certain presently preferred embodiment as including a computer programmed to run a plurality of modules comprising a feature expansion module, a weight table module, a consolidation module, and a map generation module. The feature expansion module contains feature operators for operating on a signal to expand the signal to form a feature map of feature segments Each feature segment corresponds to a unique representation of the signal created by a feature operator operating on the signal across an epoch. An epoch corresponds to an event occurring within a time segment. The weight table module provides a weight table having weight elements Each weight element has a weight corresponding to a feature segment of the feature map. The consolidation module provides a superposition segment by combining the feature segments of the feature map corresponding to the epoch by forming an inner product of the feature map and the weight table. The consolidation module also applies aggregators to consolidate the inner products or superposition segments into a distribution function representing an attribute over a domain reflecting a selected weight table, aggregator, and event type, corresponding to each value of the attribute. The map generation module produces an interpretation map that reflects a preferred weight table and aggregator to be applied to the signal data to characterize the event.

60 Claims, 15 Drawing Sheets

SIGNAL INTERPRETATION ENGINE

BACKGROUND

1. The Field of the Invention

This invention relates to signal processing and, more particularly, to novel systems and methods for pattern recognition and data interpretation.

2. The Background Art

Environmental data and stimuli have been the subject of much study for the purpose of organizing, interpreting and making useful for a future application the information that can be learned from the data.

Some sources of data that have captured the interest of those skilled in the art include neural functions. A neurocognitive adaptive computer interface method and system based on on-line measurement of the user's mental effort is described in U.S. Pat. No. 5,447,166. This method appears to be a neural network algorithm trained on data from a group of subjects performing a battery of tasks to estimate neurocognitive workload. It seems to represent a very specific algorithm trained on group data to estimate another very specific cognitive feature of brainwaves. It does not appear to be a general purpose method of analyzing all brain activity, nor does it appear to have broad application outside the tasks on which it was trained.

An electroencephalic neurofeedback apparatus for training and tracking of cognitive states is described in U.S. Pat. No. 5,406,957. This patent describes the basic invention of the mind mirror which is commercially available. The brainwave signal is Fast-Fourier-Transformed and the resulting frequency bands are displayed on a computer. The display and signal are used for biofeedback purposes but the signal is not classified or interpreted.

A brainwave directed amusement device was developed as described in U.S. Pat. No. 5,213,338 in a patent that details an arousal-level detection algorithm which is used to provide simple control of a video game. The algorithm measures the intensity (by amplitude) of raw brainwaves or a particular frequency band which varies in amplitude with the degree of arousal or relaxation a player experiences. This device is similar to other products on the market that use arousal-level to control a video game. The algorithm which provides this type of control appears limited to emotion-based arousal-level estimation and is correspondingly capable of only simple control through changes in the amplitude of one or two frequency bands from one or two sensor channels. These types of algorithms are typically limited to providing control based on brainwave arousal level or Galvanic Skin Response (GSR), also known as skin conductivity. This type of algorithm may provide a functional polygraph for lie detection and emotional arousal-level monitoring.

U.S. Pat. No. 5,392,210 concerns the localization or estimated reconstruction of current distributions given surface magnetic field and electric potential measurements for the purpose of locating the position of electrophysiological activities. The patent describes a method of getting closer to the source activity, but does not seem to provide a system of analysis or classification or interpretation of that source activity.

A method and device for interpreting concepts and conceptual thought from brainwave data and for assisting diagnosis of brainwave dysfunction is described in U.S. Pat. No. 5,392,788. This patent describes an analysis of Average Evoked Potentials by comparing the measured Evoked Potentials to the size and shapes of model waveforms or Normative Evoked Potentials, yielding from the comparison an interpretation. However, the system averages data, and requires an a priori model to be constructed for a diagnosis to be possible.

BRIEF SUMMARY AND OBJECTS OF THE INVENTION

In view of the foregoing, it is a primary object of the present invention to provide a novel apparatus and methods for signal processing, pattern recognition, and data interpretation.

It is also an object of the present invention to find attributes of a signal that may be correlated with an event associated with the same time segment as the signal where correlations are found by manipulating the signal data with various operators and weights to "expand the signal" into many different features.

Further, it is an object of the present invention to process each signal piece or segment occurring over a time segment to determine correlations between a known event and a particular, processed "feature segment."

It is still a further object of the present invention to determine optimal ways to manipulate a signal for purposes of distinguishing an event from the signal.

In addition, it is an object of the present invention to learn from at least two patterns or two event types derived from data collected from a series of related chronological events.

Another object of the present invention is to analyze complex data, from whatever source (see below for exemplary sources), and classify and interpret the data.

Consistent with the foregoing objects, and in accordance with the invention as embodied and broadly described herein, an apparatus called a signal interpretation engine is disclosed in one embodiment of the present invention as including a computer programmed to run a plurality of modules comprising a feature expansion module, a consolidation module, and a map generation module.

The feature expansion module contains feature operators for operating on a signal to expand the signal to form a feature map of feature segments. Each feature segment corresponds to a unique representation of the signal created by a feature operator operating on the signal across an epoch. An epoch corresponds to a time segment or to an event occurring within a time segment. The invention further comprises a weight table module that provides a weight table having weight elements. Each weight element has a weight corresponding to a feature segment of the feature map.

The consolidation module provides a superposition segment that combines the feature segments of the feature map corresponding to the epoch by forming an inner product of the feature map and the weight table. The consolidation module also applies aggregators to consolidate the inner products into a distribution function representing an attribute over a domain reflecting a selected weight table, aggregator, and event type, corresponding to each value of the attribute. The map generation module produces an interpretation map that reflects a preferred weight table and aggregator to be applied to the signal data to characterize the event.

A method for providing an interpretation map may include the steps of providing signal data corresponding to an event; expanding the signal data by applying a feature operator to create feature segments; providing a weight table comprising weight elements. Each weight element having a weight for adjusting the relative influence of each of the feature segments with respect to one another; superimposing one or more feature segments to provide a superposition segment by means of forming an inner product of feature segments and weight elements; aggregating the superposition segment to a attribute value; organizing attribute values from many epochs to provide a distribution function relating a value to an event type, an event instance, a weight table, an aggregator operator; and generating an interpretation map reflecting parameters for optimizing the feature expansion, consolidation, and classification of signal data into event types.

The signal data for the apparatus or the method can be derived from a medical context, a research context, and an industrial context. The medical context can be a disease, a physical impairment, a mental impairment, a medical procedure, or a therapy or treatment. The disease can be cancer, autoimmunity, a disease related to a cardiovascular condition, a viral infection, a neurological disease, a degenerative disease, a disease correlated with aging, or a disease correlated with stress. The research context can be single-trial analysis, cognitive study, psychology, neurology, cardiology, oncology, study of sleep, study of breathing, study of body conductance, study of body temperature, plant study, insect study, animal study, pharmaceutical drug-effect study, population study, flow study, physical environment study, geology, seismology, astronomy, medical clinical research, molecular biology, neuroscience, chemistry, or physics. The industrial context can be individual identification for security purposes, drug evaluation and testing, lie detection, vehicle vibration analysis, temperature diagnostics, fluid diagnostics, mechanical system diagnostics, industrial plant diagnostics, radio communications, microwave technology, turbulent flow diagnostics, sonar imaging, radar imaging, audio mechanism, yield optimization, efficiency optimization, natural resource exploration, information exchange optimization, traffic monitoring, spatial interpretation, or toxicology.

The interpretation map generated by the apparatus or the task performed by the method can provide a control mechanism based on an event or series of events selected from the group consisting of rehabilitation, biofeedback, real-time and hands-free control of virtual and real objects, mind mouse and thinking cap for controlling objects, neural controlled devices and video games, muscle controlled devices and video games, conductivity controlled video games using skin conductance, hands-free voice-free computer assisted telepathy, communication for the deaf, mute, blind or severely disabled, or a mechanism aiding prosthetic use and control.

The interpretation map generated by the apparatus or the task performed by the method can generate a prediction based on an event or series of events comprising an area of observation and monitoring selected from the group consisting of meteorology, a stock market, geology, astronomy, seismology, genetics, neurology, cardiology, or oncology. The apparatus further includes a computer display, and the method further provides using a computer display. Additionally, the invention provides a method of labeling signal data by event type.

Further, the invention is a method of creating useful applications of the signal interpretation engine, the method comprising measuring and recording events and event types, measuring and recording signal data, establishing a correspondence between an event and a signal data epoch, labeling signal data epochs by event type, using labeled signal data epochs in a learning system to generate an interpretation map, using signal data and the interpretation map in a classification system to produce interpretations, and using the interpretations to provide a useful result.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

Figure 1:
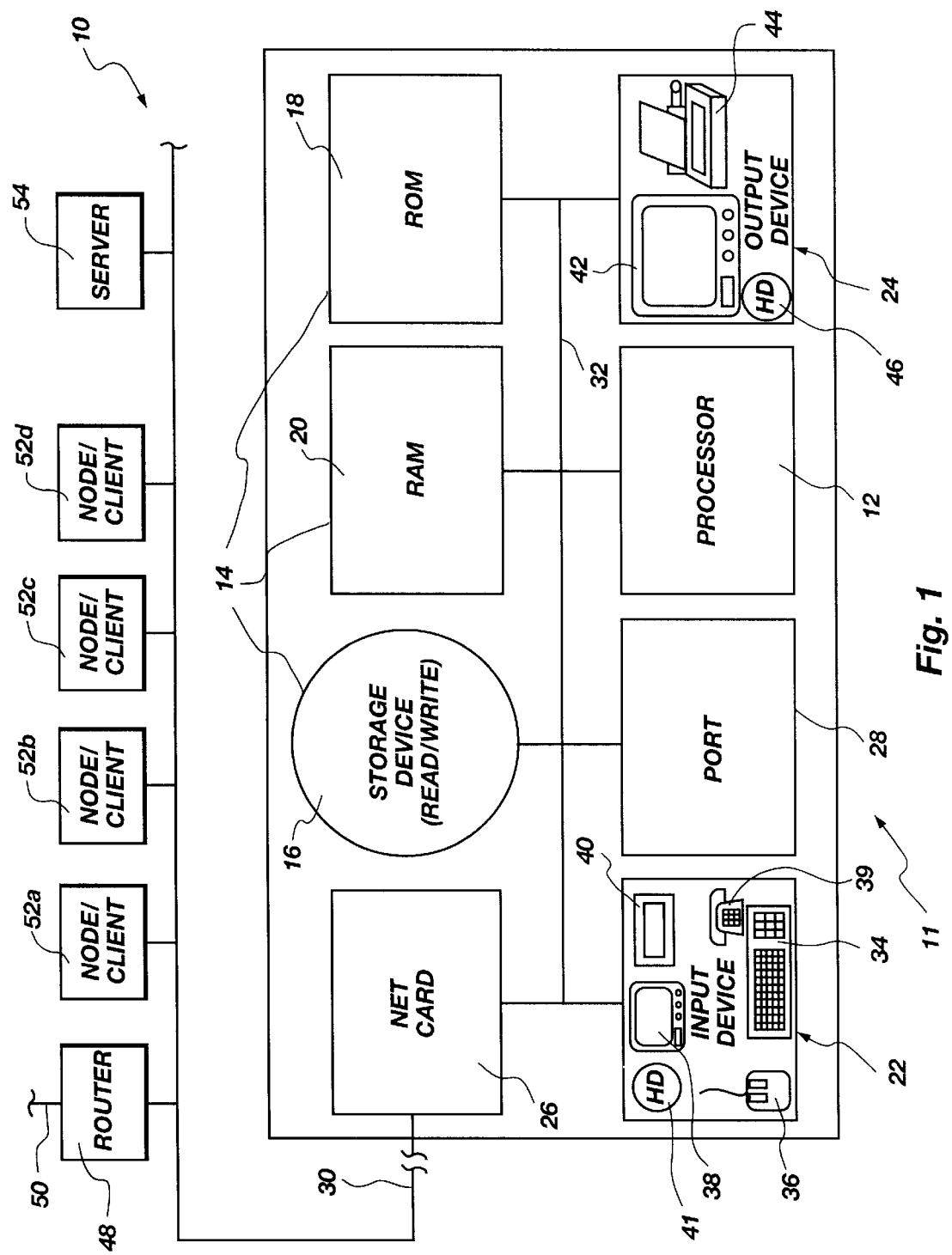
FIG. 1 is a schematic block diagram of an apparatus consistent with a hardware implementation of the invention.

The inventor has developed an apparatus and a method for interpreting data collected from a series of time points for use in a variety of applications depending on the source of the collected data. The apparatus is called a signal interpretation engine. The present invention is general purpose and easy to use in an automatic fashion. It can specifically take into consideration as few or as many features or attributes of the signal data streams as the user desires.

The invention has a learning system and a classification system and may also have other supplemental parts that prepare data for the learning and classification systems. The signal interpretation engine is capable of creating, from signal data, a set of consolidators, and can also identify which subset of consolidators is optimal or the best for the program. The consolidators can be, for example, consolidators that encode multiple physical or mathematical features, properties or characteristics. The signal interpretation engine first generates and then transforms classifications, state probabilities, and state interpretations into useful interpretations, predictions, and device control signals to drive computer objects, displays, mouse, keyboard, sound cards, and other device drivers useful to human or machine users.

The signal interpretation engine can be made increasingly accurate by increasing the dimensions (number of channels) or quality (sampling rate and signal-to-noise ratio) of the signal data that feeds it. Greater accuracies are typically achieved, for example, by increasing the number of channels, the independence of the channels, the sampling rate, the bit depth, considering more features, and using more varied features. To increase the speed of interpretations for control applications, one can use highly optimized functions to implement the apparatus or method or to implement it in special purpose parallel hardware.

Less features can be employed to speed the rate at which interpretations can be made. Employing less features may be optimal with systemically time consuming features. As dimensions, features, and quality go down, speed can dramatically increase at the expense of accuracy. As features and quality increase, the accuracy can increase dramatically, but such accuracy may be at the expense of speed. The optimum combination of features, and quality can be easily adjusted to optimize the particular application at hand to achieve a useful combination of sufficient speed and sufficient accuracy. It is acknowledged that the manipulations of the signal interpretation engine and method elements will be common place and expected for a particular application, in order to make the apparatus and method function appropriately and optimally for a given application.

The signal interpretation engine is designed so that it can automatically tune itself to the data and classification task at hand. Two or more data sets serve as examples, and from these examples the signal interpretation engine can automatically create accurate maps for use by the classification system. The signal interpretation engine is designed to train on example data more rapidly than other methods such as traditional neural networks. The signal interpretation engine maps are generally more powerful, accurate, and useful than other maps created by other methods. The interpretation maps contain explicit, easy to understand information about which signal channels, streams, locations, frequencies, times, time-lags, frequency lags, and phase relationships are most important for a given state discrimination task.

The signal interpretation engine can be applied to interpretation, control and prediction applications. The engine also has an auto-calibration or optimizing system which employs a distribution function which is composed from the data itself. The engine has a self-tuning system in which optimal subsets of high-contrast consolidators are automatically discovered from among a larger set of potential or candidate consolidators.

The signal interpretation engine is connected into (or used within) a computer with sufficient speed and available computer memory such that it can readily be made to simultaneously learn from and interpret an arbitrary high number of independent or semi-independent signal channels. The method can use the same components as the apparatus for accomplishing the method. The signal interpretation engine can use information from every time-point of every channel to analyze each time-point of each particular channel. The signal interpretation engine can uncover, capture, and discover the presence of complex patterns that are distributed across many channels, frequencies, times, and/or other features simultaneously.

The signal interpretation engine and method can find those attributes of data that are most important for discrimination and accurate classifications. The signal interpretation engine has system instances that are generally amenable to expansion to include additional feature types to be weighted separately to obtain even higher classification accuracies.

The signal interpretation engine and method can be self-tuning from the multiple contrasting data sets in the context of multiple feature types (for example: channels, locations, frequencies, times, space-lags, time-lags, frequency-lags, phase, phase-relations, and others). For example self tuning can be used to create accurate probabilities in the context of letting both space and frequency, and/or other features, receive distinct weight elements. Multiple as used herein is defined as two or more. The signal interpretation engine is product of the combination of both auto-calibration by the learning system, and self tuning by sorting, and optimal selection in the context of the use of multiple feature weights (weight table elements), multiple types of feature weights, multiple weight tables, and multiple aggregators. The signal interpretation engine can employ the simultaneous combination of all of the above features, or various combinations of a portion of them.

The signal interpretation engine includes two component parts: the learning system and the classification system. Each of these systems take input data and produce output data. The learning sequence begins with signal data bound to event types. An example of such data can be electric brain potentials. This data is calibrated and possibly time-stamped thus becoming raw signal data. The same data, in a different process, is given an event label, for example, if the data is electric brain potentials, the label could be for the subject to think "intend right" or "intend left". This event labeled data is then event identified, and possibly time-stamped, to create labeled events. Both the event data and the raw signal data are fed into a data binding module or labeler that cuts, shapes and separates these two bodies of information into labeled time segments A and labeled time segments B. These labeled time segments A and B are then processed by the learning system which is also then provided with a feature map of the features which are used to create the original data. The learning system uses a feature expander or feature decomposer to generate A feature segments and B feature segments. A and B feature segments are used to make a set of candidate consolidators consisting of weight tables and aggregators. Inner products are formed between the weight tables and the feature segments to generate superposition segments. The superposition segments are aggregated into attribute values or characteristics which are sorted and used to construct a distribution function. Distribution functions corresponding to distinct event types are used as input functions to a goal operator which generates a event type set membership function or typing confidence function. The typing confidence function is used to construct classification reliability tables. A discrimination expression is used to create a satisfaction function as a function of consolidator from the classification reliability tables. A discrimination criteria is used with the satisfaction function to select an optimal subset of consolidators. The optimal consolidators and associated corresponding functions and parameters are selected and saved to form a useful signal interpretation map. The signal interpretation map has an optimal weight table subset, an optimal subset of corresponding aggregators, a corresponding subset of distribution functions and optimal typing confidence functions, an optimal feature map, signal processing parameters, map integration parameters, and possibly other elements.

Meanwhile, a classification system takes an interpretation map and non-associated signal data as input. By using the information contained in the interpretation map, the signal data is parsed or segmented into distinct data segments or epochs and a classification executable is used to generate interpretations, probabilities and classifications. The non-associated signal data segments are fed into a feature expander to generate feature segments. These feature segments are then collapsed or superposed to generate superposition segments. An aggregator generates attribute values from these superposition segments, and a typing confidence function maps these attribute values into one or more types of interpretations. The interpretations can be probabilities, memberships, classifications, predictions, or control signals, depending on the particular data or end use.

The interpretations which are the end result of the work of the learning system and the classification system, are pattern presence indicators, pattern interpretations, meanings, pattern presence probabilities, event types, classes, states, conditions, event predictions, control signals, categorizations, or segment classifications, depending on the nature of the original data and the intended use for that data. These types of results generated by the signal interpretation engine (by the work of the learning system and the classification system) can be applied to one of the following: an interpreter, a controller, or a predictor, or a method for interpreting, controlling or predicting The interpreter generates interpretations suited to use by an end user. The controller generates control signals to control something for a user. The predictor generates predictions for an end user.

The apparatus and method may be implemented in various embodiments to accomplish a wide variety of tasks. Generally, the apparatus and the method may learn from a series of chronological events and associated signal data. This learning is encoded in an interpretation map which is the output of the learning system. The classification system takes an interpretation map as input along with non-associated signal data and uses the map to interpret the signal data into useful interpretations such as event types.

The signal data stream may come from any source. Exemplary sources are demonstrated by exemplary applications to which the signal interpretation engine method and apparatus can be directed, for example, an application to a specific task. The task can be, for example, using signal data to develop an interpretation of an event or series of events, using signal data to provide a control mechanism for an event or series of events, or using signal data to generate a prediction based on an event or series of events. The interpretation can be made using data from a medical context, a research context, or an industrial context. Control mechanisms can be provided for entertainment, rehabilitation, or assisting the disabled, for example. Predictions can be based from observation and monitoring in areas including meteorology, stock market analysis, geology, astronomy, seismology, genetics, neurology, cardiology, and oncology, for example.

The interpretation of an event or series of events can include applying the invention to signal data containing information derived from a medical context, a research context, or an industrial context. The medical context can be a disease, a physical impairment, a mental impairment, a medical procedure, or the context of a therapy or treatment. The disease can be, for example, cancer, autoimmunity, a disease related to a cardiovascular condition, a viral infection, a neurological disease, a degenerative disease, a disease correlated with aging, and a disease correlated with stress.

The information can be derived from a research context including the contexts of single-trial analysis, cognitive study, psychology, neurology, cardiology, oncology, study of sleep, study of breathing, study of body conductance, study of body temperature, plant study, insect study, animal study, pharmaceutical drug-effect study, population study, flow study, physical environment study, geology, seismology, astronomy, medical clinical research, molecular biology, neuroscience, chemistry, or physics.

Where the information is derived from an industrial context including, for example such contexts as individual identification for security purposes, drug evaluation and testing, lie detection, vehicle vibration analysis, temperature diagnostics, fluid diagnostics, mechanical system diagnostics, industrial plant diagnostics, radio communications, microwave technology, turbulent flow diagnostics, sonar imaging, radar imaging, audio mechanism, yield optimization, efficiency optimization, natural resource exploration, information exchange optimization, traffic monitoring, spatial interpretation, or toxicology.

Where the task comprises providing a control mechanism for an event or series of events, the control can be for the purpose of rehabilitation, biofeedback, real-time and hands-free control of virtual and real objects, mind mouse and thinking cap for controlling objects, muscle and neural controlled devices and video games, conductivity controlled video games using skin conductance, hands-free voice-free computer assisted telepathy, communication for the deaf, mute, blind or severely disabled, or a mechanism aiding prosthetic use and control.

Where the task comprises generating a prediction based on an event or series of events the prediction can be made in an area of observation and monitoring including for example, meteorology, a stock market, geology, astronomy, seismology, genetics, neurology, cardiology, and oncology.

In all cases, the information that is derived within the specific context is derived in the form of a signal, for example electrical potential measurements made in the specific context, or any other measure of activity or change. These measurements can be taken by an electrode, a sensor, a computer, a record keeping facility, by other methods appropriate in the specific context, or by any combination of these methods. The information will be appropriate to the specific context, for example, where the signal interpretation engine or the method of the invention are used in a cardiac context, heart activity will be the information that forms the signal data. Similarly, where the context is a neurological context, brain activity (for example brain waves) will form the signal data.

In other biological contexts, other body waves, or potentials, for example skin or muscle potential may be used. In a biological research context for example signal data can be collected by sensors. Particular sensors can be used in a variety of tissue and cellular contexts, including for example, the sensors described in WO 96/38726, EP 745, 843, EP 743,217, and U.S. Pat. No. 5,585,646. In an industrial context, signal data can be derived as is appropriate for the industry being studied or monitored. In a control context, signal data is derived from the control context, for example where enabling the disabled to effect control is the goal of the apparatus of method, signal data will be generated from the disabled body in order to effect the desired control through the apparatus or method. In a prediction context, for example in predicting the weather, seismological activity, or a stock market activity, signal data is derived from past events and used to predict future events. Further exemplification of the various contexts from which signal data can be derived, and to which the apparatus or method of the invention can be applied is made below. In all cases the simple principle remains the same: that signal data is derived as is appropriate for the activity, and that data is fed into the apparatus or used to practice the method.

Further examples of applications of the signal interpretation engine and method follow. Radio waves can be processed by the signal interpretation engine for making, for example, radio astronomy interpretations, radio communications studies, and microwave studies. In addition chemical activity interpretation, earth quake prediction, vibration analysis, acoustic and sound analysis and interpretation, oil exploration and prediction, biological activity interpretation of plants, cells or animals can be achieved with the apparatus and method of the invention.

Other medical applications include, for example, multiple sclerosis myelin regeneration therapy via biofeedback from interpretations tuned to signal myelin growth and decay. Novel therapies for other chronic, autoimmune, and neurological disorders can also be developed using the signal interpretation engine. In addition, novel technologies involving the development of somatic-autonomic connections and applications can be constructed using the signal interpretation engine, for example, letting autonomic physiology label brainwaves and using the signal interpretation engine to construct autonomic maps. Further applications include anesthesia depth monitoring before, during and after surgery, and epileptic spike and seizure precursor detection.

In the entertainment field, for example, the signal interpretation engine can be used to achieve real-time and hands free control of virtual and real objects. Mind mouse and thinking cap products can be developed which use brainwaves to control objects, including computer games, for example A thinking cap can be developed using the signal interpretation engine for other control applications Neural and muscle controlled video games can also be developed, and can be used, for example, for simultaneous exercise and entertainment for health and computer enthusiasts. Conductivity controlled video games using galvanic skin response, epidermal response, or skin conductivity pathways through the body, can be developed using the signal interpretation engine.

In the realm of communications, for example, hands-free voice-free computer assisted telepathy can be developed using the signal interpretation engine, and communications systems for deaf, mute, or otherwise disabled persons having communications difficulties can also be developed.

In a prediction context, for example, weather and stock market predictions can be made using the signal interpretation engine. For example, local and global weather prediction from ground and satellite data can be determined. Local weather predictions can be made from interpretation of signal data packets or data segments from sensors placed in the environment. Solar flare predictions can be made. Solar proton event prediction can be made to alert power grid companies and satellite communication companies. Earthquake predictions can be made, as well as other environmental monitoring conducted. Ocean currents and temperatures can also be predicted.

In a market context, for example, prediction of one event of one security or index from a stock market can be accomplished. Predictions can be made by analyzing the simultaneous signal data of many stocks, funds, commodities, rate derivatives, or futures with the signal interpretation engine. Market or economic information, economic trends, commerce transactions, internet traffic, and other signal data can be used to create market maps. These market maps can be used by the signal interpretation engine to create predictions and interpretations of market transactions and currency flows, for example.

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 15, is not intended to limit the scope of the invention, as claimed, but it is merely representative of the presently preferred embodiments of the invention.

The presently preferred embodiments of the invention will be best understood by reference to the drawings, wherein like parts are designated by like numerals throughout.

Referring now to FIG. 1, an apparatus 10 may include a node 11 (e.g., client 11, computer 11) containing a processor 12 or CPU 12. The CPU 12 may be operably connected to a memory device 14. A memory device 14 may include one or more devices such as a hard drive or other non-volatile storage device 16, a read-only memory 18 (ROM) and a random access (and usually volatile) memory 20 (RAM).

The apparatus 10 may include an input device 22 for receiving inputs from a user or another device. Similarly, an output device 24 may be provided within the node 11, or accessible within the apparatus 10. A network card 26 (interface card) or port 28 may be provided for connecting to outside devices, such as the network 30.

Internally, a bus 32 may operably interconnect the processor 12, memory devices 14, input devices 22, output devices 24, network card 26 and port 28. The bus 32 may be thought of as a data carrier As such, the bus 32 may be embodied in numerous configurations. Wire, fiber optic line, wireless electromagnetic communications by visible light, infrared, and radio frequencies may likewise be implemented as appropriate for the bus 32 and the network 30.

Input devices 22 may include one or more physical embodiments. For example, a keyboard 34 may be used for interaction with the user, as may a mouse 36. A touch screen 38, a telephone 39, or simply a telephone line 39, may be used for communication with other devices, with a user, or the like. Similarly, a scanner 40 may be used to receive graphical inputs which may or may not be translated to other character formats. The hard drive 41 or other memory device 41 may be used as an input device whether resident within the node 11 or some other node 52 on the network 30, or from another network 50.

Output devices 24 may likewise include one or more physical hardware units. For example, in general, the port 28 may be used to accept inputs and send outputs from the node 11. Nevertheless, a monitor 42 may provide outputs to a user for feedback during a process, or for assisting two-way communication between the processor 12 and a user. A printer 44 or a hard drive 46 may be used for outputting information as output devices 24.

In general, a network 30 to which a node 11 connects may, in turn, be connected through a router 48 to another network 50. In general, two nodes 11, 52 may be on a network 30, adjoining networks 30, 50, or may be separated by multiple routers 48 and multiple networks 50 as individual nodes 11, 52 on an internetwork. The individual nodes 52 (e.g. 52a, 52b, 52c, 52d) may have various communication capabilities.

In certain embodiments, a minimum of logical capability may be available in any node 52. Note that any of the individual nodes 52a–52d may be referred to, as may all together, as a node 52.

A network 30 may include one or more servers 54. Servers may be used to manage, store, communicate, transfer, access, update, and the like, any number of files for a network 30. Typically, a server 54 may be accessed by all nodes 11, 52 on a network 30. Nevertheless, other special functions, including communications, applications, and the like may be implemented by an individual server 54 or multiple servers 54.

In general, a node 11 may need to communicate over a network 30 with a server 54, a router 48, or nodes 52. Similarly, a node 11 may need to communicate over another network (50) in an internetwork connection with some remote node 52. Likewise, individual components 12-46 may need to communicate data with one another. A communication link may exist, in general, between any pair of devices.

In one embodiment, an apparatus 10 and method 121, in accordance with the invention, may process data provided from a signal generator or signal source (e.g. one or more of any suitable type of input device 22), whether connected directly to the bus 32, or external to the apparatus 10. Thus, a signal source may be a signal generator, data acquisition system, digital signal processor, sensor, measurement apparatus, or the like, operably connected to the apparatus 10 through the port 28 or the network 30.

Such a signal source may be a peripheral device (schematically represented by the port 28 itself) connected through the port 28. Alternatively, such a signal source may be connected to the network 30 as a node 52 (e.g. any of the nodes 52a, 52b, etc.). The signal source may connect to the apparatus 10 through yet another network 50, or may simply provide data to a memory device 14 by any method known in the art.

Figure 2:
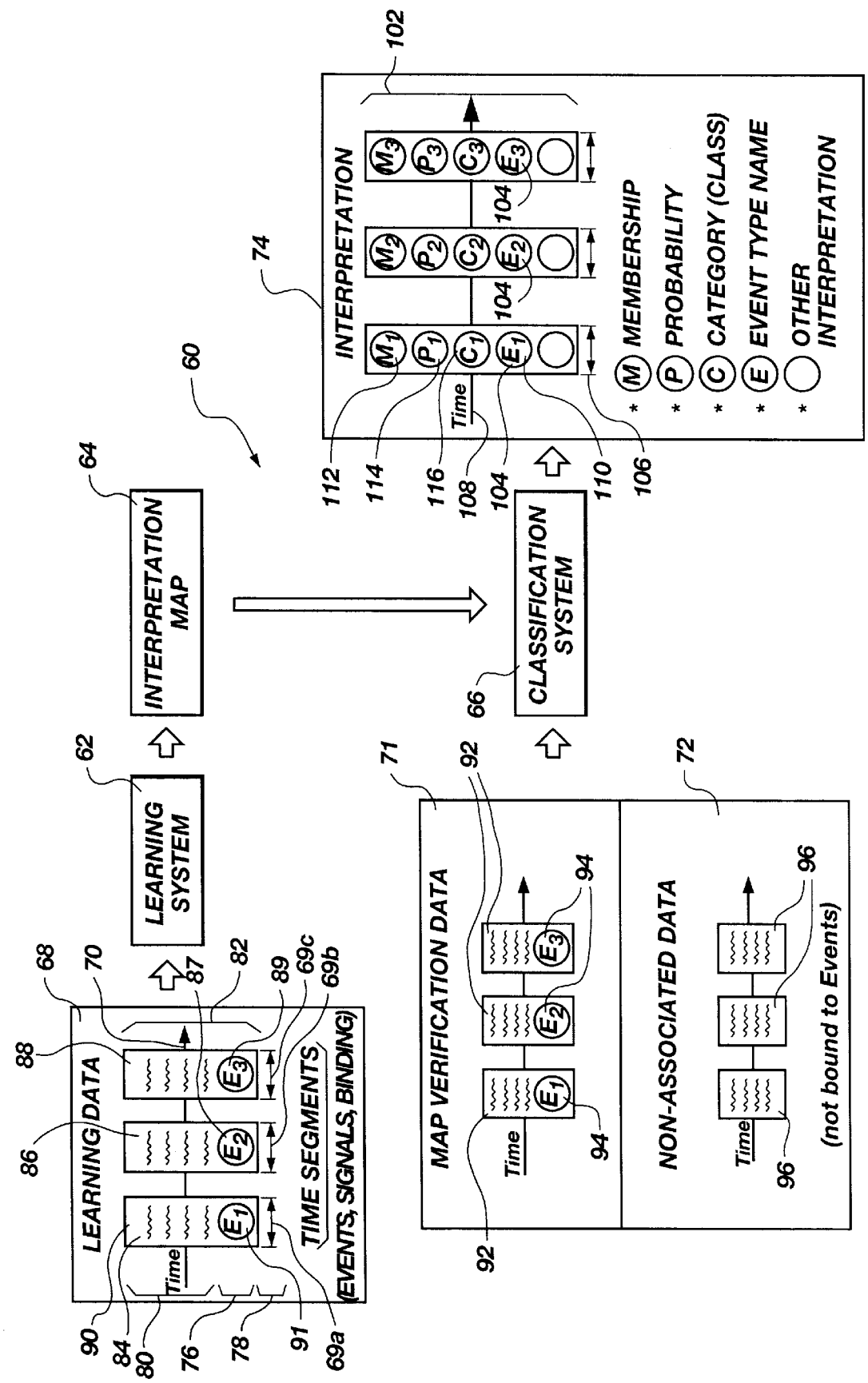
FIG. 2 is a schematic block diagram of an interpretation engine in accordance with the invention.

Referring now to FIG. 2, a schematic block diagram is shown illustrating an interpretation engine 60 implemented in the apparatus 10 of FIG. 1. The interpretation engine 60 may include a learning system 62 for providing an interpretation map 64. The interpretation map 64, when used by a classification system 66 may interpret data of unknown origin. The learning system 62 may receive learning data 68 taken over time 70. The learning system 62 creates an interpretation map 64 using the learning data 68. Using the interpretation map 64, a classification system 66 may operate on map-verification data 71 to verify the accuracy, reliability, or discrimination capability of the interpretation map 64.

The classification system 66 may be embodied in software modules (e.g., see FIG. 3 et seq.) executing on a processor 12. In one presently preferred embodiment, the classification system 66 and the learning system 62 may be comprised of the same modules 120 connected to form a method 121. The classification system 66 operates on data structures, such as the non-associated data 72. Non-associated data 72 does not have identifiable events bound thereto. Thus, event types or events may be predicted by the classification system 66 to correspond to the non-associated data 72. By contrast, the learning system 62 is tasked with associating event types 76 and signal data 80 to form the interpretation map 64.

Ultimately, an interpretation 74 is provided by the classification system 66.

Referring to FIG. 2, events 76 may be identified with some phenomenon of interest. Typically, an event 76 is a classically observable event. For example, a physical act such as raising a hand, moving a thumb, or the like, may be classified as an event. An event 76 typically occurs over or during some time segment 78. Physical phenomena occur in a time domain 70. Meanwhile, signal data 80 may be provided from an input device 22 or from some other device connected to an apparatus 10.

Signal data 80 may be segmented or subdivided into epochs 82. The epochs 82 may correspond to individual time segments 78, each with a corresponding event 76. For example, the event 91 corresponds to the several channels 84 in the epoch 90. Other epochs 86, 88 correspond to different events 87, 89. For example, several signal generators, signal sources, or several different signals from one or more sensors may be provided as data. Each individual signal may be thought of as one of the channels 84. Thus, each epoch 86, 88, 90 corresponds to a respective event 87, 89, 91 occurring during, before, after, over, or with some relationship to a particular time segment 69a, 69b, 69c. Nevertheless, the time segments 69 (a generalized time segment, on which the individual time segments 69a, 69b, 69c are specific instances) need not be exclusive. For example, the time segments 69a, 69b may overlap one another. In another embodiment, some gap may exist between the time segment 69a and time segment 69b. Thus, the epochs 82 need not span the entire time 70 from which the time segments 69 are extracted.

In FIG. 2, the verification data 71 may include epoch data 92 corresponding to particular events 94. Binding of data 92 to events 94 was similarly done for the learning data 68 used by the learning system 62. Thus, the verification data 71 provides verification by the classification system 66 of the interpretation map 64 obtained from the learning data 68. In one embodiment, the verification data 71 may be the same as the learning data 68. However, in another embodiment, the verification data 71 (map-verification 71) may be independent from the learning data 68. Thus, the classification system 66 operating on the verification data 71 may highlight errors in the accuracy or reliability of the interpretation map 64.

By contrast, the non-associated data 72 may have epoch data 96 having no known corresponding events 76. Accordingly, the classification system 66 must be relied on entirely to provide an interpretation 74 identifying appropriate events 76. The interpretation 74 may include several individual interpretations 102 or outputs 102. For example, the classification system 66 may provide events 104 or event types 104 corresponding to particular time segments 106. The time segments 106 represent either exclusive or non-exclusive portions of a time 108 or time continuum 108.

For example, a particular instance 110 or event 110 may be thought of as a particular occurrence of some phenomenon in time and space that is unique. Nevertheless, the event instance 110 may be a particular instance of some general event type 104.

Corresponding to the particular instance 110 may be a membership 112, a probability 114, a category 116, a state, a class, a condition, a type and the like. Each of the interpretation variables 112, 114, 116 may be thought of as information useful to a machine, process, or user. For example, membership 112 may actually reflect a degree of presence or membership as understood in fuzzy set theory, a grade or level of any characteristic of an event type 104 in a particular epoch 82. Similarly, a category 116 may be an event type. For example, a hierarchy of event types may include such functions as a body movement, a right or left side body movement, an upper or lower appendage movement, an arm movement, a forearm movement, an upward forearm movement, and the like at any level of distinction. More subtly, a particular event may occur in an unobservable mode. For example, a thought or emotion may occur. Nevertheless, signal data 80 may be generated by such an event.

One may keep in mind that an event type 104 may be an array or a vector. For example, a single event type 104 may be composed of several sub-events. In one embodiment, an event type 104 may be a composite event type. This prospect is particularly true when tracking body movements. In one example, a human being may move an index finger. The index finger may be moved upward, downward, left, right, or the like. Likewise, the index finger may be moved in coordination with an opposing thumb, and another finger. Moreover, many useful motions may correspond to motion of several fingers and a thumb along with a hand and an arm to execute a particular motion. As prosthetic applications for the interpretation engine 60 abound in such biomechanical applications as prosthetic members, very complex event types 104 may be useful. These event types may be represented as vectors composed of many subelements, many degrees of motion, speeds of motion, and the like.

Figure 3:
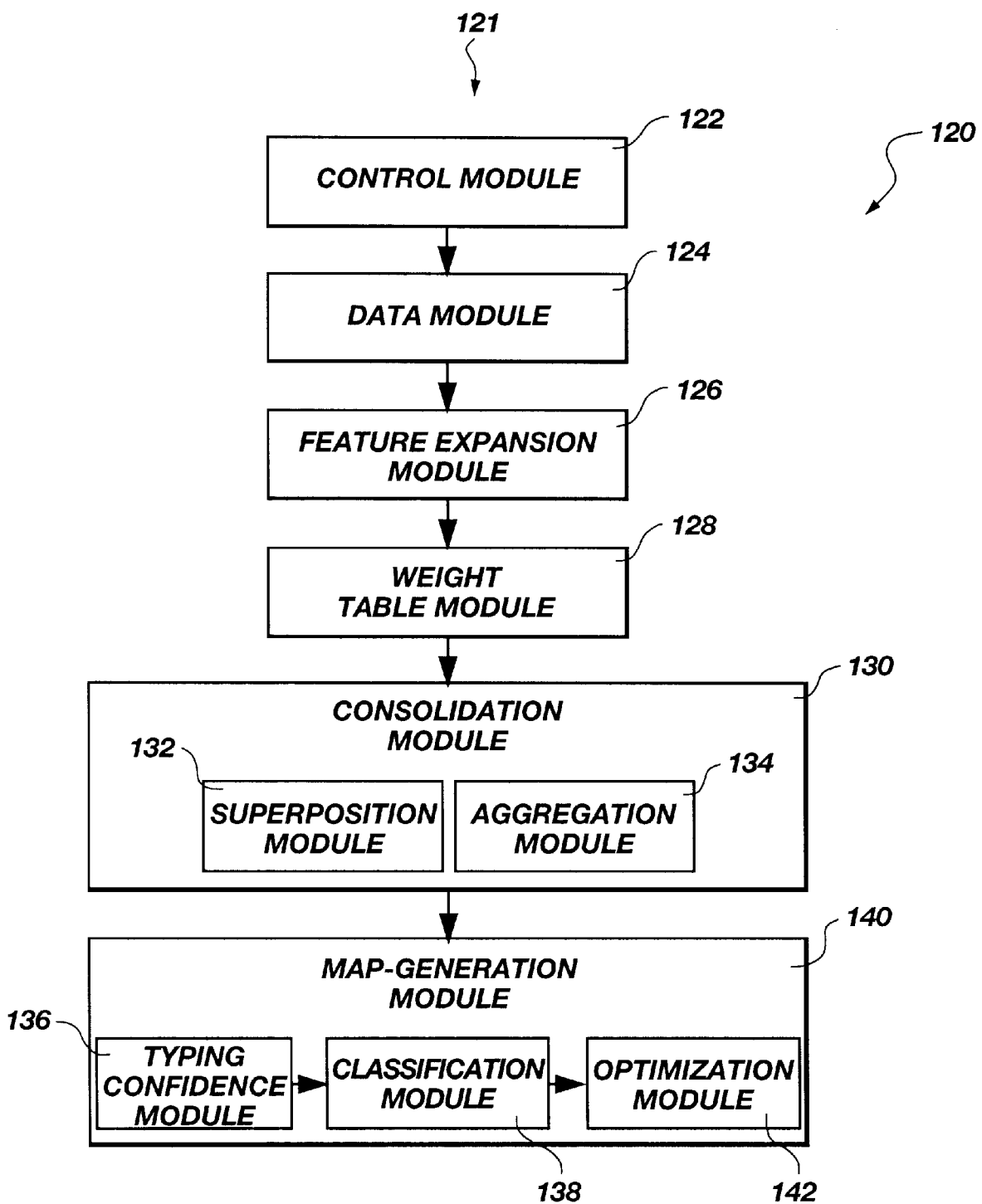
FIG. 3 is a schematic block diagram of a method in accordance with the invention, implementing modules for executing on an apparatus of FIG. 1.

Referring now to FIG. 3, modules 120 are combined to form a process 121. In one presently preferred embodiment, a control module 122 may provide for the execution and support of the other modules 120. A data module 124 may provide the inputs as well as user selections for executing the method 121. A feature expansion module 126 may operate on data 68, 71, 72 to expand particular phenomena of individual data channels 84, combinations of channels 84, or individual attributes drawn therefrom for further processing by the method 121.

A weight table module 128 may provide weight tables for adjusting the particular influence of any particular output from the feature expansion module 126. For example, phase relationships may be adjusted to accommodate the particular location of time segments 69 relative to channel data 84.

A consolidation module 130 may consolidate the multiplicity of data that has been generated by a feature expansion module 126 over one or more weight tables (see FIG. 7) generated by the weight table module 128. Thus, the feature expansion module 126 operates to increase the number of data segments derived from any particular epoch 82 corresponding to a time segment 69. By contrast, the consolidation module 130 operates by way of a superposition module 132 to combine data. Moreover, an aggregation module 134 may operate before or after a superposition module 132. The aggregation module provides aggregator operators to further consolidate data from a particular epoch 82 to a single value characterizing an epoch 82.

A map-generation module 140 may use data provided by the consolidation module 130 to create the interpretation map 64. The map-generation module 140 may be implemented, in one embodiment, to include a typing confidence module 136 to establish a level of confidence (degree of membership, degree of presence, etc.) with which an event type 104 may be properly bound (associated, classified, represented by, etc.) to a particular epoch 82 for which channel data 84 has been provided.

A classification module 138 may provide a measure of reliability contributed by a consolidation module 130 to a classification process. When executing the classification module 138, the learning system 62 compares true event types with event types that have been classified or predicted using particular selections made in the consolidation module 130. By contrast, the classification system 66, when executing the classification module 138, may either verify the interpretation map 64 against known data having events 94 bound to epoch data 92, or may simply predict event types 104 based upon non-associated data 96.

The map-generation module 140 may include an optimization module 142 that actually produces the interpretation map 64. The optimization module 142 may be thought of as reviewing and evaluating the selections and processes occurring in the feature expansion module 126, weight table module 128, consolidation module 130, and the previous modules 136, 138 from the map-generation module 140. The optimization module 142 selects parameters that best provide accurate classification and discrimination according to criteria selected for distinguishing particular event types 104. Thus, the optimization module 142 may provide a final interpretation map 64 that uses the best underlying parameterization of processes and features of the method 121 and modules 120.

Figure 4:
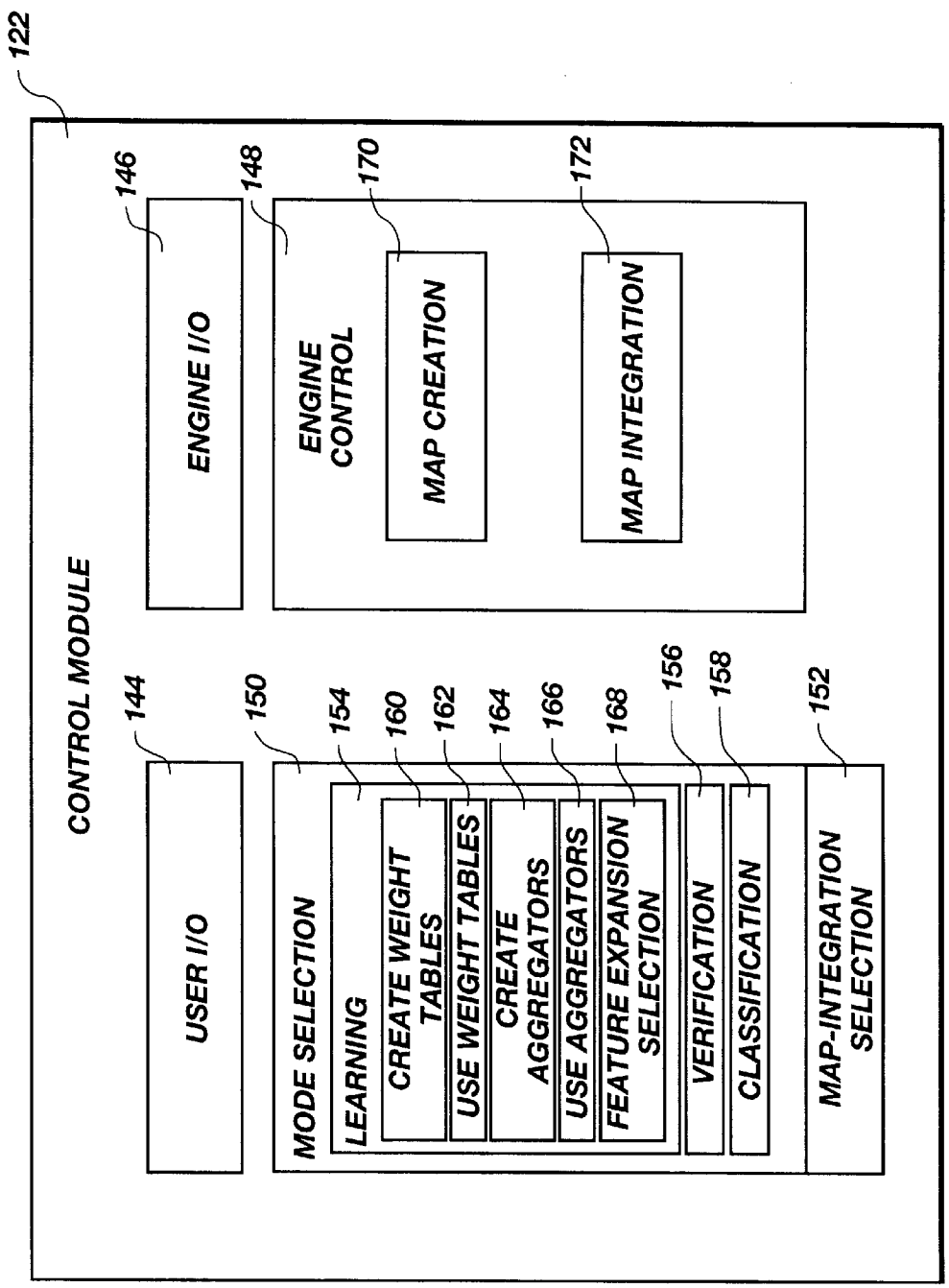
FIG. 4 is a schematic block diagram of a control module embodiment of FIG. 3.

Referring now to FIG. 4, a control module 122 may include a user I/O module 144. The user I/O module may provide for interaction with a user. For example, the input devices 22 may communicate through the user I/O module 144. Similarly, an engine I/O module 146 (engine I/O 146) may interface between the control module 122 and other functions of the process 121.

The control module 122 may contain an engine control module 148 for controlling the sophistication and repetition of operation of the learning system 62 and classification system 66 in providing interpretation maps 64 or interpretations 74. The control module 122 may also include a mode selection module 150, as well as a map-integration selection 152.

A mode selection module 150 may provide for user selection of various modes for executing the learning system 62 and classification system 66. For example, a learning menu selection 154, a verification menu selection 156, and a classification menu selection 158 may be provided for selecting various modes of operation for the learning system 62 and the classification 66. The learning menu selection 154 may include other selections 160, 162, 164, 166, 168. For example, a create weight tables selection 160 may provide for creation of a weight table through one mode of operation of the weight table module 128. By contrast, the use weight tables selection 162 may provide a different operation of the weight table module 128.

Similarly, a create aggregators selection 164 may provide for operation of one mode of the aggregation module 134. The use aggregators selection 166 may cause the aggregation module 134 to operate in another mode. The feature expansion selection 168 may control operation of the feature-expansion module 126.

Typically the verification selection 156 may cause the classification system 66 to rely on the map-verification data 71 for operation. By contrast, the classification selection 158 may cause the classification system 66 to rely on the non-associated data 72 for operation.

An engine control module 148 may provide a map creation module 170 for outputting the interpretation map 64. However, in one embodiment of an apparatus and method in accordance with the invention, an interpretation map 64 may be but one of many interpretation maps that are to be integrated into an integrated interpretation map. Just as events may be made up of other subevents, a super map 64 may be a combination of many other interpretation maps 64. Thus, a map integration function 172 may be provided for such complex events and combinations of events.

In general, the control module 122 may provide several other functions in either the user I/O module 144 or the mode selection module 150. For example, various preliminary signal processing may occur for the learning data 68, map verification data 71, and non-associated data 72. Accordingly, a user may select in the user I/O module 144 a particular set of signal processing parameters. In another embodiment of an apparatus and method in accordance with the invention, the mode selection module 150 may include other sub-modules or selection menus for identifying and selecting signal processing parameters to be used in a particular execution of the learning system 62 or classification system 66.

Figure 5:
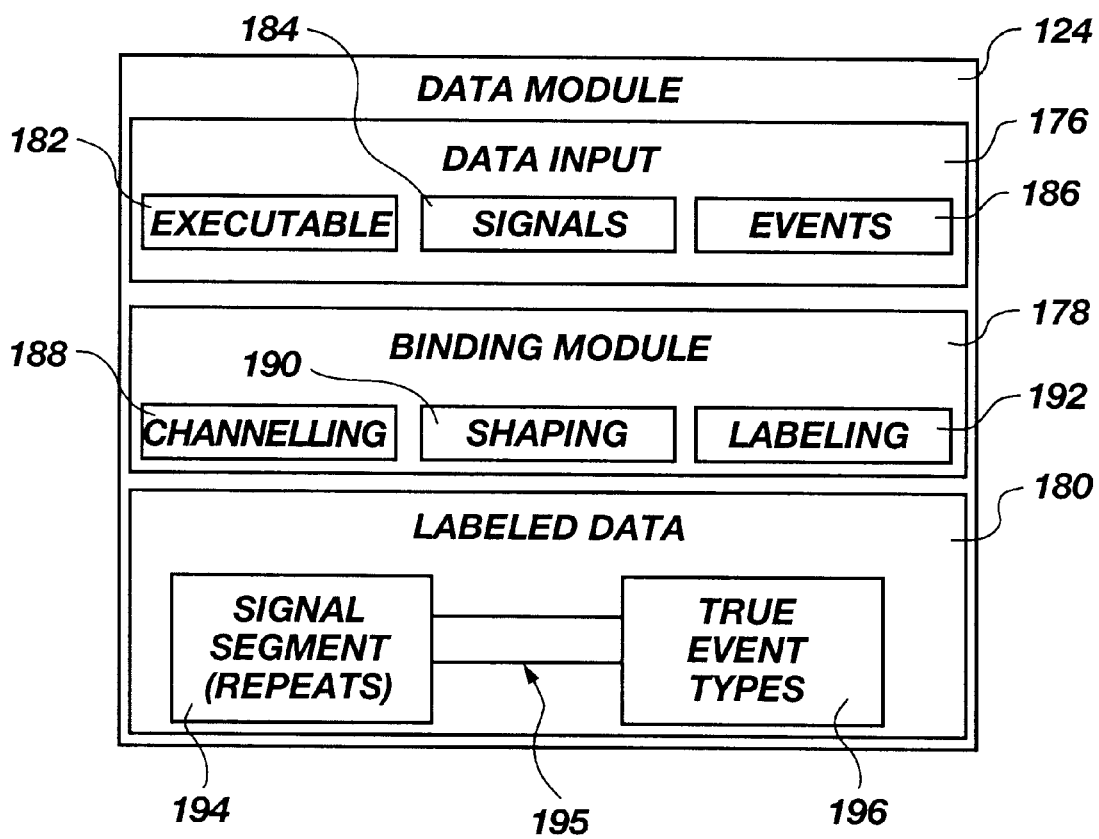
FIG. 5 is a schematic block diagram of a data module embodiment of FIG. 3.

Referring now to FIG. 5, the data module 124 may include a data input module 176, a binding module 178, and labeled data 180. Of course, logical grouping of executables and data may occur in other embodiments. However, from a logical point of view, the functional provisions of the data module 124 may be illustrated by this architecture. The data input module 176 may contain one or more executables 182 for moving, accumulating, selecting, parsing, shaping, segmenting and otherwise manipulating data. For example, the executables 182 may contain a parse function or parser whose operation is to select, cut, and/or shape signal segments from a continuous stream of input signal data 72 and store or make available these signal segments to the classification system 66. Similarly, signals 184 or signal data 184 may be stored as a data structure within a data input module 176. Events 186 or event data 186 may also be stored as a data structure. The executable 182 may provide instructions to the processor 12 for moving the signal data 184 and event data 186 into and out of the data input module 176.

The binding module 178 which may include a channeling module 188 may determine what channels 84 are to be included, used, and defined as input signal data. For example, an individual signal sensor may provide a data stream which may be further manipulated and subdivided into more than a single channel. Thus, in general, a signal sensor may actually provide one or more channels for evaluation. For example, phase relationships, time lags, maxima, minima, averages, and the like may all be extracted from a single signal. Thus, the raw data corresponding to some voltage or other output of a signal sensor may be provided as a particular channel identified by the channeling module 188. Moreover, such a channel may also be accompanied by several other channels representing other manipulations or viewpoints of the same or related data.

A shaping module 190 may provide several functions, such as parsing, segmentation, and shape-weighing of individual epochs 82 by time segment 69, and other signal processing. For example, the shaping module 190 may ascertain phase or time relationships between individual events 76 and their associated signal data 80. Likewise, between the channeling module 188 and the shaping module 190, the signal data 80 may be manipulated to present phase-related, frequency-related, and other parameter-based data corresponding to a particular epoch 82. Thus, any particular relationship between time, frequency, signal values, latencies, phases, and the like may be provided.

A labeling module 192 may provide binding between events 76 and their corresponding signal data 80. Moreover, the labeling module 192 may provide binding between any processed data provided from the channeling module 188 and shaping module 190 to a particular event type 104, time segment 78, epoch 82, and the like.

An output of the data module 124 may be labeled data 180. The labeled data 180 may include signal segments 194 corresponding to individual epochs 82. Accordingly, true event types 196, corresponding to events 76 provided in the learning data 68 may be bound by binding data 195 to the signal segments 194. The binding data 195 may be by virtue of actual tables, indices, matrices, databases, or any other binding mechanism known in the art. Accordingly, the true event types 196 and signal segments 194 may exist in virtually any domain and range corresponding to an epoch 82. Thus, the distinction between an event 76, event type 196, and signal segments 194 may be thought of as being somewhat arbitrary. That is, once a signal may be detected and defined, it may be regarded as an event in its own right.

Figure 6:
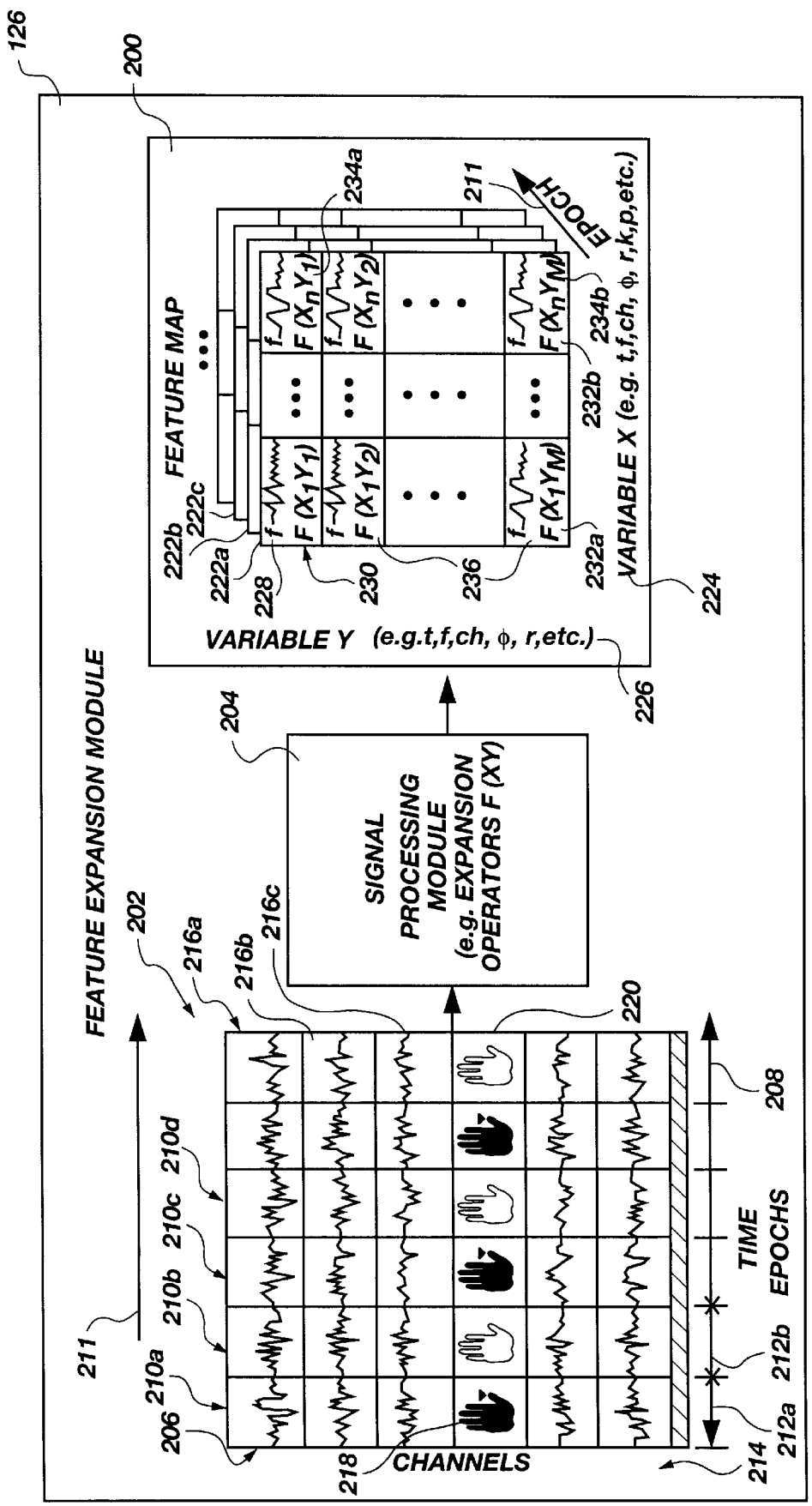
FIG. 6 is a schematic block diagram of a feature expansion module embodiment of FIG. 3.

Referring now to FIG. 6, a feature expansion module 126 may provide a feature map 200. Moreover, the feature expansion module 126 may actually use the feature map 200 for further processing. The feature map 200 may be developed using the signal data 202 following certain signal processing in a signal processing module 204.

A channel 206 may provide data over some time continuum 208. The time continuum may be subdivided to define epochs 210 (e.g., 210a, 210b, 210c, etc.), each corresponding to a particular time segment 212 (e.g., 212a, 212b, etc.). All of the individual epochs 210 define an epoch domain 211 made up of all of the individual epochs 210. The epoch domain 211 may be as significant as the time domain 208 in defining events 76.

The several channels 214 (e.g., channel 206) may each provide particular channeled data 216 (e.g., 216a, 216b, 216c, etc.). Moreover, the channel data 216 may be associated with event data 220 or event type data 220. The event data 220 may be provided by transducers measuring a physical phenomenon of interest. Alternatively, event data 220 may be input through an input device 22 by a user. Thus, a concurrent input through an input device 22 may establish the bounds of an event 76 defined by event data 220.

A principal function of the signal processing module 204 is to provide the feature map 200. The feature map 200 may be thought of as several feature maps 222 (e.g., 222a, 222b, 222c, etc.) corresponding to several epochs (210a, 210b, 210c, etc.). For example, considering the case of just two variable types X and Y, a feature map 222 may include an X 224 or variable X 224 and a Y 226, or variable Y 226 forming a domain. For each combination of X 224 and Y 226, a feature segment 228 may be provided. The feature segment 228 is an output of a feature operator 230 or F 230 corresponding to a particular X 224 and a particular Y 226. For example, the $X_1$ 232a, to the $X_n$ 232b may vary across several values of a particular parameter type represented by the variable X 224. For example, variable X 224, and variable Y 226 may be selected from several parameters including time, frequency, channel number, phase, moment, distance, time lag, wave number, spatial frequency, frequency lags, spatial lags, and the like. Moreover, the variables X,Y 224, 226 may represent a maximum, minimum, mean, inflection point, slope, weighted integral, wavelet index or coefficient, and any other signal processing parameter known in the art.

A principal function of each of the variables X,Y 224, 226 is to render explicit (or reveal) data that may be implicit (or hidden) within signal data 202 corresponding to a particular epoch 210. Thus, one may think of plotting a variable 226 against another variable 224. Thus, some relationship may appear. Meanwhile, a frequency, for example, may be plotted against a phase lag, or against a time segment, or other variable to simply provide a binding relationship. The significance or insignificance of such a relationship will be evaluated later by an apparatus and method in accordance with the invention.

A feature segment 228, represented by the function designated with a lower case letter f, in the feature map 222a is an output corresponding to a feature operator 230 represented by an upper case letter F.

Meanwhile, a variable $Y_1$ 234a through a variable $Y_m$ 234b may span values of the variable Y 226 in a feature map 222. Each of the feature maps 222a, 222b, 222c, may correspond to a particular epoch 210a, 210b, 210c. Thus, an epoch domain 211 moves through many epochs 210, each having a corresponding feature map 222 of the overall feature map 200. One may think of each feature map 222 as containing a single set of feature operators 230 applied to data from a different epoch 210 in each case. Thus, the feature map 222a and the feature map 222b will correspond to the same set of operators 230 for each value of the variable X 224 and variable Y 226 in the feature map 222. However, the feature segment 228 for each element 236 in the feature map 222a will be different from the corresponding feature segment 228 in the corresponding element 236 of the feature map 222b.

The feature map 200, as illustrated in FIG. 6, shows a two-dimensional domain in X 224 and Y 226. Nevertheless, in general, any individual feature map 222 may exist in a space of any dimension, involving as many variables 224, 226, as desired. Each of the feature maps 222 may, accordingly, be quite sparsely populated. That is, not every variable 224, 226 need necessarily imply the existence of every other variable 224, 226 or feature operator 230. Also, one may note that in general, for example, a particular variable 224, 226 may be a particular function or type of function or parameter, such as frequency. Accordingly, each individual instance 232a, 232b, 234a, 234b, may be a particular value of an underlying parameter type 224, 226 over some domain of interest.

In general, feature operators 230 for creating the feature map 200 may expand from or collapse to any symplectic space, or any other time, frequency, position, or wavevector-related space. Such spaces may include generalized time-frequency and space-wavevector distributions. Wigner functions and wavelet distributions fit this category.

Figure 7:
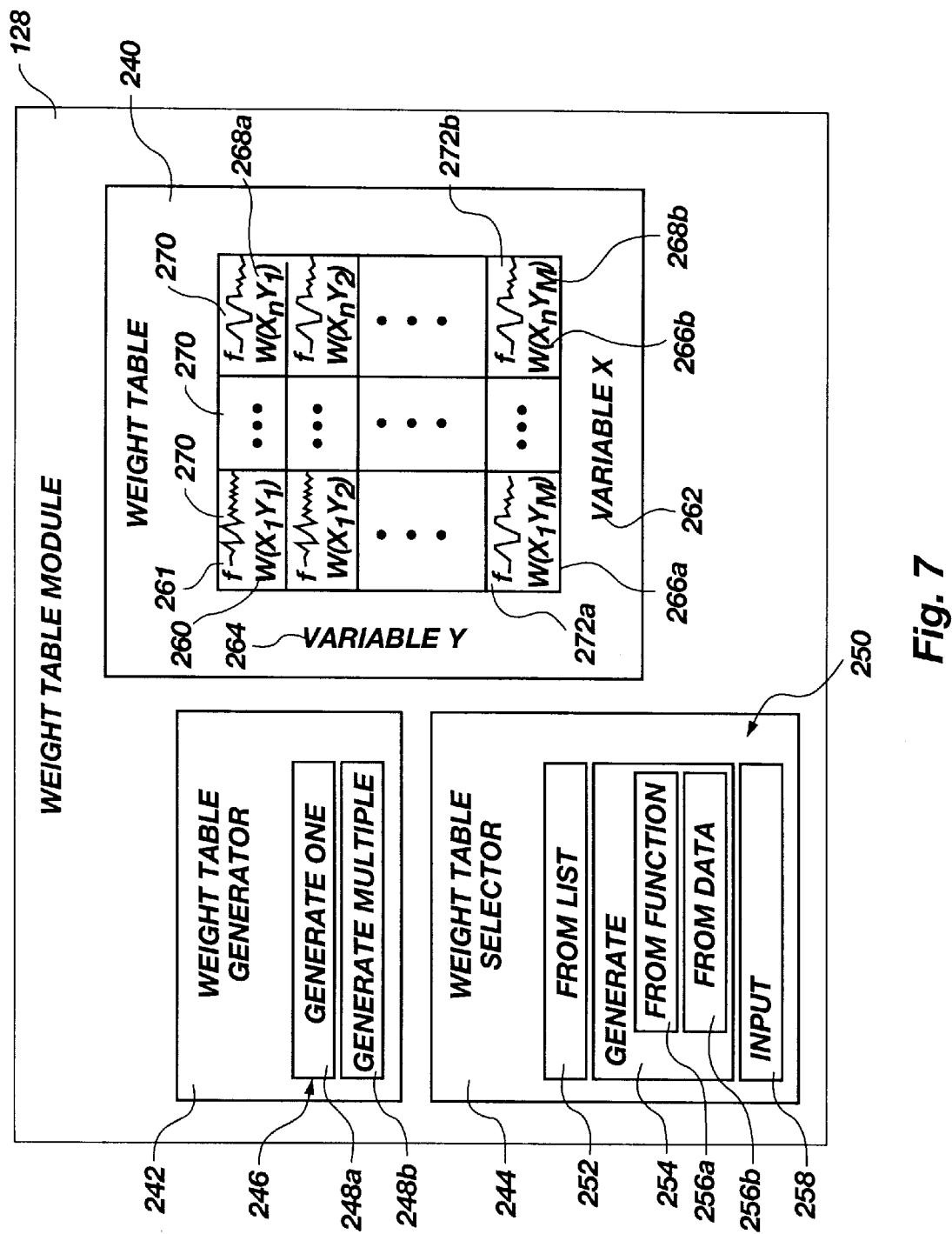
FIG. 7 is a schematic block diagram of one embodiment of a weight table module of FIG. 3.

Referring now to FIG. 7, a weight table module 128 may provide a weight table 240. The weight table 240 may be provided by a weight table generator 242, in one presently preferred embodiment. However, in an alternative embodiment, a weight table selector 244 may provide a weight table 240 from a previous execution of a weight table generator 242, or from some other input.

A menu 246 may provide to a user a choice, including a selection 248a to generate a single weight table 240. Alternatively, a selection 248b may generate multiple weight tables 240. The multiple weight tables 240 may correspond to various, different methods for generating weight tables 240. For example, a weight table may be composed of a constant in every instance. Alternatively a weight table may be based on some distribution, such as a balancing distribution to maximize the influence of data corresponding to the center of a time segment 212 of an epoch 210.

In another embodiment, a weight may be based on some manipulation of the data 216 of an epoch 210 that will tend to self-neutralize. For example, certain resonance frequencies may occur at a higher or lower frequency than the background noise. Thus, shifting data 216 slightly forward or backward within a time segment 212 and adding or multiplying the data 216 together may provide enhancement of certain features, while minimizing others relative thereto Thus, in general, several approaches to a weight table 240 may be implemented. Accordingly, a user may elect the selection 248b to try several different weight table generation approaches.

The weight table selector 244 may include a selection 252 containing a list from which a weight table 240 may be provided apriori. Similarly, a selection 254 may indicate that a weight table generator 242 is to be invoked to generate a weight table 240, or a collection of weight tables 240 from an executable, input signal data, other data, pre-programmed function, or the like. For example, a selection 256a may indicate that a weight table 240 is to be generated from a function. Similarly, a selection 256b may indicate that a weight table 240 is to be generated from data provided in the weight table selector 244 according to functions that may be selected to operate thereon. Also, a selection 258 may provide for a weight table 240 to be input directly, element-by-element, function-by-function, data with a function, or in some other appropriate input format. In one embodiment, a random number generator may actually generate a range of weights to be placed in a weight table 240 such that the process 121 may simply select a best number of the random numbers.

One principle of operation in selecting a method of operation for a weight table generator 242, which may be included in a selection 252, 254, 258 of the weight table selector 244, may be to generate a weight table 240 in which the individual weights will span the same variables 224, 226 as the feature map 200. In one embodiment, building a weight table 240 using the learning data 68 itself, is to take individual feature segments 228 and manipulate them to highlight particular features. For example, a feature segment 228 may be thought of as a wave function. Accordingly, the wave function may be integrated, differentiated, presented as a weighted integral, such as wavelet coefficient, analyzed for moments of area, mean, maxima, and the like. In one approach, a feature segment 228 may be used as a foundation for a matrix of integrals correlating feature segments 228 against themselves, against each other, keeping track of individual epochs 82 and binding data 195 relating the feature segments 228 to the time segments 69, 212 and the event types 76. In one embodiment, Wigner functions, Choi-Williams functions, or other time-frequency joint distribution, such as wavelet distributions, and generalized time-frequency distribution functions may be used to build operators to operate on the feature segments 228 in order to provide a weight table 240. In one embodiment, feature segments 228 may be manipulated by centered Fourier transforms, convolutions, and the like. Such manipulations may be used to form operator representations or matrix representations of feature segments 228 or the underlying data 216.

In one embodiment of an apparatus and method in accordance with the invention, weight tables 240 may be generated by embedding feature segments 228 into statistical matrices or operators by one of several available methods.

Typical methods may include, for example, covariance matrices, correlation matrices, data matrices, Wigner function matrices, and other time-frequency distribution matrices. Typical time-frequency distribution matrices should typically be capable of statistically representing information corresponding to feature segments 228 within an epoch 82 of interest. Given statistical matrices, it may be valuable to label each statistical matrix according to those epochs 82 to which it is being applied for creating weight tables 240. The binding data 195 relating each event 220 and event type to an epoch 82, 210 should likewise be bound to the statistical matrix.

Just as a particular event or event type may be one of a larger class of event type, the statistical matrices may be likewise be nested by event type and subtype. In particular, matrices may be combined into polynomials reflecting addition, subtraction, multiplication, and division of statistical matrices. Each statistical matrix may benefit from being labeled or bound to one or more event types. Statistical matrices may be related by products and ratios of their respective elements. In general, matrices may be multiplied and divided element-by-element, or may be multiplied and divided as matrix-by-matrix to produce another matrix. It is preferable, in one embodiment of an apparatus and method in accordance with the invention, to bind each matrix to a respective event type. Again, event types and matrices may be nested as types, subtypes, and the like.

Matrices built up from other matrices may be referred to as composition matrices. Composition matrices may be further analyzed by one of several methods. Selected methods may include, for example, singular value decomposition, known in the mathematical art, eigenvalue analysis, generalized eigenvalue analysis, principal component analysis, or the like, to extract singular vectors and eigenvectors characterizing and corresponding to embedded statistical information relating two or more event types to one another.

A set of singular vectors or eigenvectors, may be considered together as a set of vectors. A set of vectors may be used to provide multiple weight tables 240. Thus, a list of weight tables 240 may be applied, for purposes of selecting a best weight table 240 used in the superposition module 132 for creating the superposition segments 280.

Weight tables 240, regardless of method for generating them, may be refined and improved by one of several well-understood methods. For example, the method of steepest descent, and other optimization methods may select a best weight table 240 from a space populated by weight tables 240 to select a greatest, least, or otherwise best weight table 240. In general, any optimization technique may be used. For example, a brute force method may simply analyze all weight tables 240 in a space populated and spanned by weight tables 240. The method of steepest descent operates more efficiently, so long as local variations in an analyzed function (of weight tables 240) do not obscure global minima and maxima. The operation of optimization methods is well understood in the art.

In general, a method and apparatus in accordance with the invention may benefit greatly from a judicious selection of weight tables 240. In the event that little understanding is available with respect to signal data 80, a variety of weight tables 240 may be selected. An apparatus and method in accordance with the invention, will then evaluate the effect of each weight table 240 to select a preferred weight table 240 providing clear distinctions between various event types 104.

In accordance with selections by a user or other executable to control the basis and creation or use of a weight table 240, a weight table 240 may be provided by a weight table generator 242. The weight table 240 may typically include several, individual weights 260, each corresponding to a specific feature segment 261 from the feature map 200. Also, each weight 260 may correspond to a particular variable X 262 and a particular variable Y 264. The variable X 262, and variable Y 264 correspond to the variable X 224 and variable Y 226 of the feature map 200.

Figure 9:
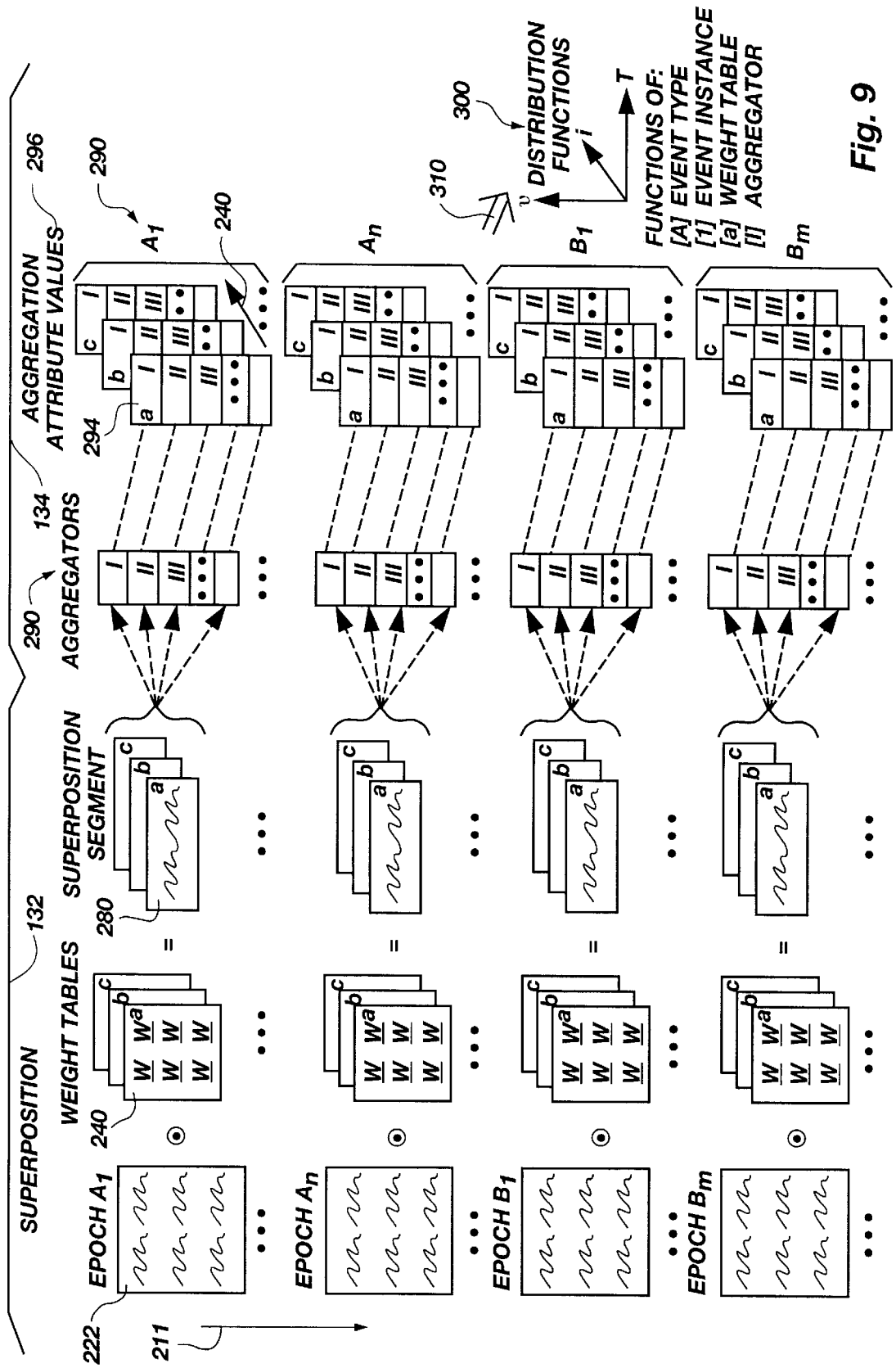
FIG. 9 is a schematic block diagram of processes including superposition and aggregation, in one embodiment consistent with the consolidation module of FIG. 8.

An individual weight table 240 may be applied to many different epochs 82, 210 in an epoch space 211 (see FIGS. 6 and 9). Thus, each of the elements 270 of a weight table 240 contains an individual weight 260 to be applied across several, perhaps even all, epochs 82, 210. In one example, a first value of X 262 may correspond to a feature such as a frequency. Accordingly, an $X_1$ 266a may represent a first value of frequency or of that particular feature of interest, while another variable X. 266b represents another value of the feature (frequency) of interest. Similarly, a particular Y 264 may represent a time lag between initiation of an event 76 and some aspect of signal data 80 represented in the feature segment 261. Accordingly, a variable Y, 268a may represent a first value of the feature (time lag in this case), while another variable Y.,, 268b may represent another value of such a feature (time lag).

A weight table 240 may actually be made up of many weight tables 240. Nevertheless, it may still be appropriate to refer to a weight table 240 as a single weight table 240. One may see that a single table 240 may be extracted from a larger matrix of candidate weight tables 240 to be tried over multiple epochs in an epoch dimension 211 or epoch space 211 containing all epochs 82, 210.

In one presently preferred embodiment, each element 270 may contain a particular weight 260 to be applied to a particular feature segment 261. The feature segment 261 may be treated as an input by a weight table generator 242, for generating weight tables 240. In an alternative embodiment, the weight 260 may be independent of the feature segment 261, but may be applied by the superposition module 132 in forming an inner product between the weight table 240 and the feature map 200. In a presently preferred embodiment, the weights 260 for each element 270 of a weight table 240 maintain identical positions over all epochs 82, 210 in an epoch space 211.

Figure 8:
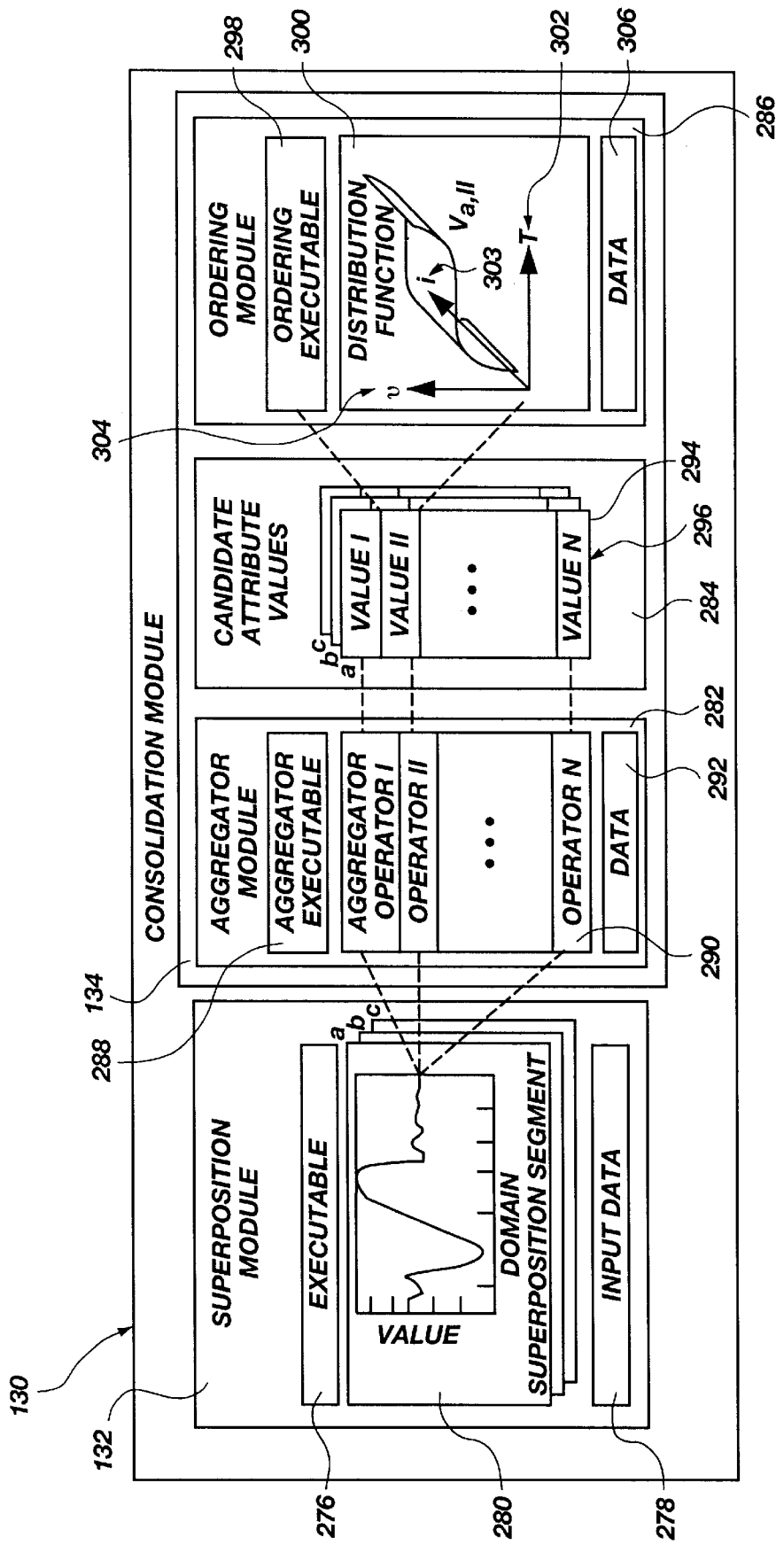
FIG. 8 is a schematic block diagram of a consolidation module in one embodiment, consistent with FIG. 3.
Figure 10:
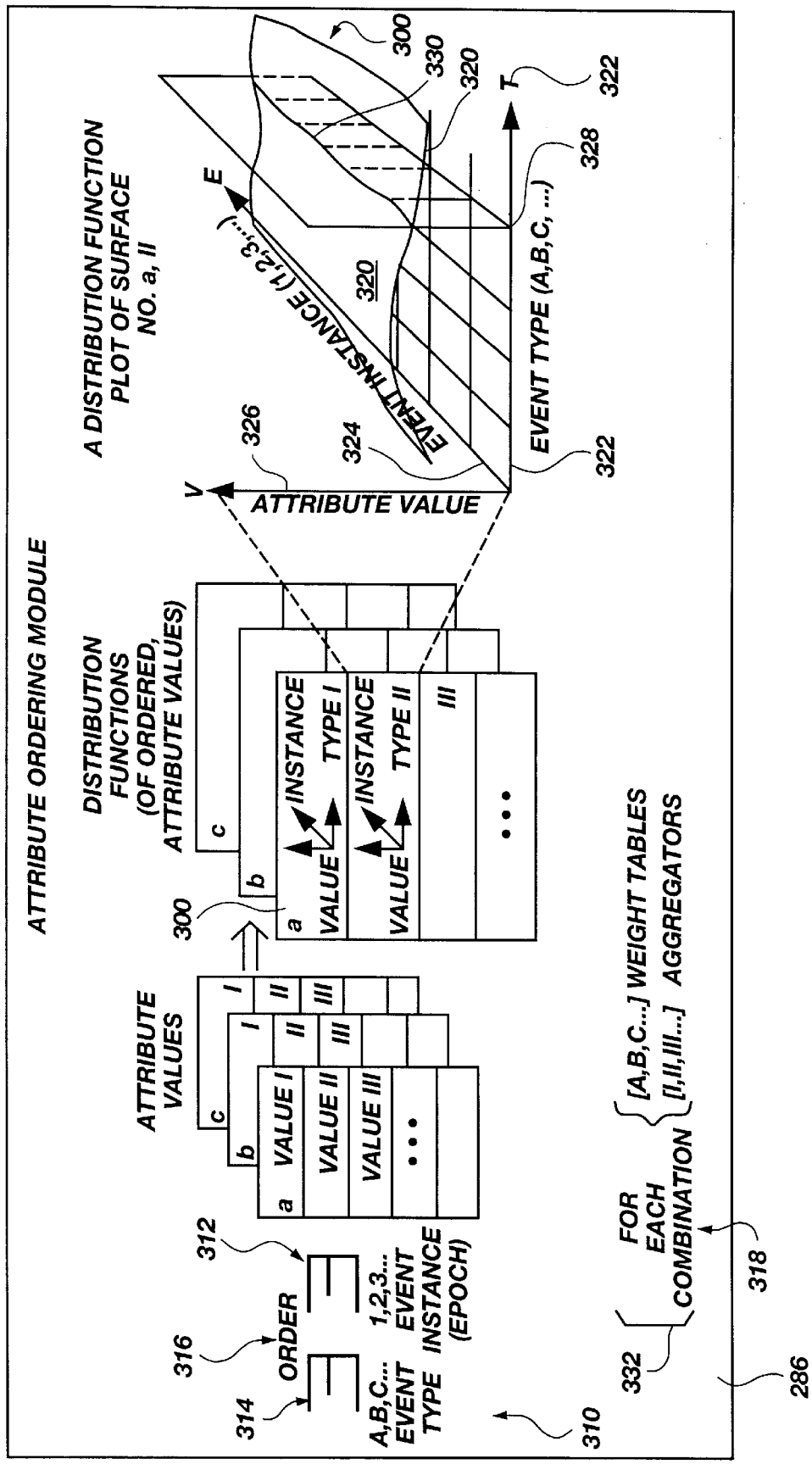
FIG. 10. Is a schematic block diagram of one embodiment of an attribute ordering module consistent with FIG. 8, and FIG. 9.

Referring now to FIGS. 8–10, and more particularly to FIG. 8, a consolidation module 130 may be implemented in several sub-modules 132, 134. In one embodiment, a superposition module 132 may include an executable 276 for operating on input data 278 to provide superposition segments 280. In general, the input data may include, for example, a feature map 200 and one or more weight tables 240. In addition, other data for supporting the executable 276 may be included in the input data 278.

A principal function of the executable 276 is to provide an inner product of the feature map 200 with a weight table 240. Referring to FIG. 6, one may note that the feature map 200 is illustrated to show a correspondence between individual feature operators 230, and corresponding feature segments 228 created thereby from the signal data 80, 216. The executable 276 forms an inner product between the feature segments 228 (wave functions 228) and the weights 260 of the weight table 240. Thus, each element of the weight table 270, is illustrated in FIG. 7 as a feature segment 261 paired with a particular weight 260 in a weight table 240. Accordingly, the executable 276 multiplies each corresponding pair of feature segments 261 and weights 260, summing all such products to form an inner product.

The executable 276, thus provides several feature segments 261 multiplied by weights 260, added together (superimposed, superpositioned) to form one, composite, superposition segment 280. If multiple weight tables 240 are applied to a feature map 200, then a superposition segment 280 corresponding to each weight table 240 may be prepared by the executable 276.

Likewise, a feature map 200 may actually comprise multiple feature maps 222. Each feature map 222 corresponds to an individual epoch 82, 210, from which signal data 80 (channel data 216) was received. Accordingly, if several epochs 210 are used for creating individual feature maps 222 in the overall feature map 200, each epoch may multiply the number of superposition segments 280. Thus, in general, a superposition segment 280 will exist for each combination of an epoch 210, and a weight table 240.

An inner product taken between a feature map 222 and a weight table 240 may be any mathematical inner product. Commonly, a mapping between elements of a first matrix and elements of a second matrix may be used to form a series of products which may be added to obtain a single value representing an inner product between the two matrices. However, other inner products may include, for example, weighted inner products, power products, involving powers other than unity for each element of one or more of the matrices involved in the inner product, and the like. One may think of a superposition module 132 as providing a summary of useful features found in the various feature segments 261, 228 into a single superposition segment 280. Thus, a superposition segment 280 contains a representation of certain accentuations of desirable data contained within many feature segments 228, 261.

FIG. 9 illustrates a superpositioning process in an epoch space 211 of multiple epochs 222 over a plurality of weight tables 240 to provide an array of superposition segments 280. In FIG. 8, an aggregator module 282 may provide attribute values 284 for use by an ordering module 286. The aggregator module 282 may include an aggregator executable 288 for performing the functions of the aggregator module, using one or more aggregator operators 290. The aggregator operators may include aggregator operators, aggregator functionals, and the like, which may be referred to as aggregators themselves, or as aggregation operators, and other names as known in the art. Each of the aggregator operators 290, or simply operators 290, may operate on data 292 in order to provide attribute values 284, 294. The data 292 may include the superposition segments 280 and other supporting data required by the executable 288 for providing the attribute values 284, 294.

In one embodiment of an apparatus and method in accordance with the invention, aggregator operators 290 may be selected from one of the many operators known in the art. Examples of operators may include, moments, attribute values, attributes, coefficients, inner products, and other properties. Other properties may be derived from integrals, weighted integrals, wavelet coefficients, moments from a mean, moments from an origin of a domain, moments of moments, mean, variance, skewness from a mean, origin, basis value, and the like. Aggregator operators 290 may be selected from any function or functional that will map a value or values in one space to a value in a space of lesser dimension. Thus, in the mathematical arts, aggregator operators exist in numerous varieties. The fundamental feature of an aggregator operator 290 is to reduce a dimension of a space representing a function. An aggregation operator 290 may reflect a selection of points or regions from a time-frequency distribution representing a superposition segment 280. In general, certain aggregation operators 290 may simply reflect a single property, such as a crossing value, a minimum value, a mean value, a maximum, minimum, slope, moment, area, or the like, characterizing or characteristic of a particular superposition segment 280.

One may note that an aggregation operator 290 may be applied, in general, to any function in any dimensional space. One may notice that an aggregator operator 290 tends to provide attribute values 284 reflecting a shape or pattern of a superpositioned segment 280. Thus, various operators 290 may tend to elicit a resonance of a particular group of superposition segments 280 to a characteristic shared, unknown, but accentuated by the particular operator 290. Thus, for example, a high, large lobe on a superposition segment 280 on a right side of a superposition segment 280 may be reflected in a moment about a vertical axis at a central lobe of a domain. Thus, such a lobe, shared by several superposition segments, may be accentuated by a moment operator 290 operating on the plurality of superposition segments 280. In general, the attribute values 284 may be combined into tables 296 of individual attribute values 294. Each table 296 may correspond to a particular weight table 240. Similarly, each of the attribute values 294 may correspond to a particular aggregation operator 290.

The ordering module 286 provides further consolidation and organization of attribute values 284. The ordering module 286 may include an ordering executable 298 for determining a nature order of placement for the attribute values 284.

The ordering executable 298 may place each individual attribute value 294 in an order, such as a monotonically ascending or descending order from greatest to least or least to greatest over some domain. For example, in one embodiment of an apparatus and method in accordance with the invention, a distribution function 300 may map (distribute, describe, represent, etc.) a domain over all event types 302 and all instances 303 of events 76. The domain, may extend over additional dimensions representing all aggregator operators 290, and all weight tables 240. Thus, in one embodiment, the domain may be four dimensional. The distribution function 300, may map the individual attribute values 294 to a value 304 or value axis 304, extending throughout the domain. Thus, a distribution function 300 may reflect a surface corresponding to all values of attribute values 294 in a domain of event type 302, event instance 303, weight table 240, and aggregator operator 290.

As illustrated in FIG. 3, the consolidation module 130 of FIG. 8 may be thought of as containing a superposition module 132 and aggregation module 134. As illustrated in FIG. 3, the superposition module 132 and aggregation module 134 may operate in any order, and may each provide outputs to the other, or their functions may be combined into a single module. For example, the superposition module 132 may provide superposition segments 280 to the aggregation module 134. The aggregation module 134 may create a distribution function 300. The distribution function 300 may be provided to the superposition module 132 for preparing better superposition segments 280. Thus, the superposition module 132 and aggregation module 134 may operate to pass superposition segments 280 and distribution functions 300, respectively, back-and-forth to one another.

In accordance with common practice for software architecture, the consolidation module 130 has been subdivided into a superposition module 132 and aggregation module 134. However, alternative configurations may provide a single consolidation module 130 integrating all of the functions of the superposition module 132 and aggregation module 134 into a single executable. Similarly, the feature expansion module 126, weight table module 128, and consolidation module 130 may be integrated into a single executable representing the process 121 implemented by all of the individual modules 120. Thus, the modules 120 represent a logical architecture for distributing the functionalities required to implement the method 121. Alternative embodiments of an apparatus and method in accordance with the invention, may provide equivalent functionality of the modules 120 in a different configuration.

Referring now to FIG. 9, the superposition module 132 and consolidation module 134 are represented. Several epochs 222 may define an epoch space 211 of all epochs 222. Accordingly, the superposition module 132 may form inner products of each epoch 222 (feature segments 228, 261 over all weight tables 240) to form superposition segments 280. All superposition segments 280 may be operated on by aggregator operators 290 to provide a multiplicity of tables 296 of attribute values 284, with the individual attribute values 294 making up all attribute values 284.

An ordering operation 310 is performed by the ordering executable 298 of the ordering module 286 to provide the distribution functions 300. Thus, each distribution function 300 may correspond to all attribute values 294 corresponding to points in a domain made up of event types, event instances, weight tables, and aggregators. Thus, the attribute values 294 vary in a fifth dimension over a four-dimensional domain of event types, event instances, weight tables, and aggregators.

Referring now to FIG. 10, the ordering operation 310 is further illustrated. The ordering operation 310 or ordering process 310 may include a universal operator 312 and universal operator 314 indicating that an order operation 316 is to occur over all event instances and event types, respectively.

Meanwhile, a combination 318 or combination operator 318 provides for combining every combination of weight tables 240 and aggregators 290 (aggregator operators 290). Thus, the combination 318 of weight tables 240 and aggregators 290 may result in corresponding distribution functions 300. The distribution functions 300 contain ordered attribute values 294. The distribution function 300 may be represented as a surface 320 extending over a domain including an event type 322 as one dimension, and an event instance 324 as another dimension. A surface 320 representing the attribute values 294 varying along an attribute value axis 326 or attribute value 326 may be created for each combination of weight table 240 and aggregator operator 290. Thus, the distribution function surface 320 is illustrated as a three-dimensional surface over a two-dimensional domain. However, the surface 320 may also be thought of as a five-dimensional surface extending over a four-dimensional domain as described.

One may think of a specific event type 328 occurring in the event type dimension 322. Correspondingly, a curve 330 represents a distribution of the attribute value 326 over the event instance 324 or event instance axis 324 at a fixed event type 328.

As a practical matter, a weight table 240 and an aggregator operator 290 need not be closely related or related at all to any other weight table 240 and aggregator 290. Moreover, a weight table 240 and an aggregator 290 may be independent from one another. Thus, a combination 318 of a particular weight table 240 and a particular aggregator operator 290 may be thought of as one consolidating pair 332 or simply as one consolidator 332. Alternatively, one may refer to a consolidator operator 332 as the data and operation of one weight table 240 and one aggregator operator 290.

One may note that the surface 320 representing a distribution function 300 need not be continuous. For example, all event instances 324 may correspond to one or a few event types 322. Similarly, some limited number of particular epochs 82, 210 may correspond to only certain event instances 324, event types 322, or both. Thus, the surface 320 may be discontinuous, even sparsely populated with attribute values 294. Thus, not every combination of a particular event type 322 and event instance 324 will have a corresponding attribute value 294. In addition, the domain of event type 322 and event instance 324 may be either a discreet or continuous domain.

A distribution function may plot several values corresponding to attribute values. However, a distribution function is created for each event type. That is, an event of a particular type may occur repeatedly. Each occurrence of the event may occur in a different time epoch. A collection of several different epochs all corresponding to different instantiations of the same event type may be combined to build several sample points or instances of an event type. Thus, each attribute value corresponds to an entire epoch (all channels over one single corresponding time segment) occurring at one instance of an event.

Thus, each collection of attribute values represents several epochs wherein the individual channels have been expanded, weighted, superposed, and aggregated into a single value corresponding to the particular epoch.

The distribution function then begins with an abscissa corresponding to epoch number in chronological order with an ordinate corresponding to the value of the attribute value. Then, all of the values of the attribute values for a particular event type (event type A, as opposed event type B) may be arranged in a monotonically ascending or descending order. Thus, the abscissa becomes an epoch number as a function of an ordinate that is a ranked value of a attribute value. The monotonic nature of the sorted values provides a defacto ranking. Moreover, the distribution function so provided may be thought of as a natural grid having a spacing by epoch number (which may be converted to a ranking number instead of the chronological number originally associated with a epoch number) and a value. Thus, each first, second, third, fourth epoch becomes a ranking number on a x axis while the values provide the ordinate values for a natural grid.

Figure 11:
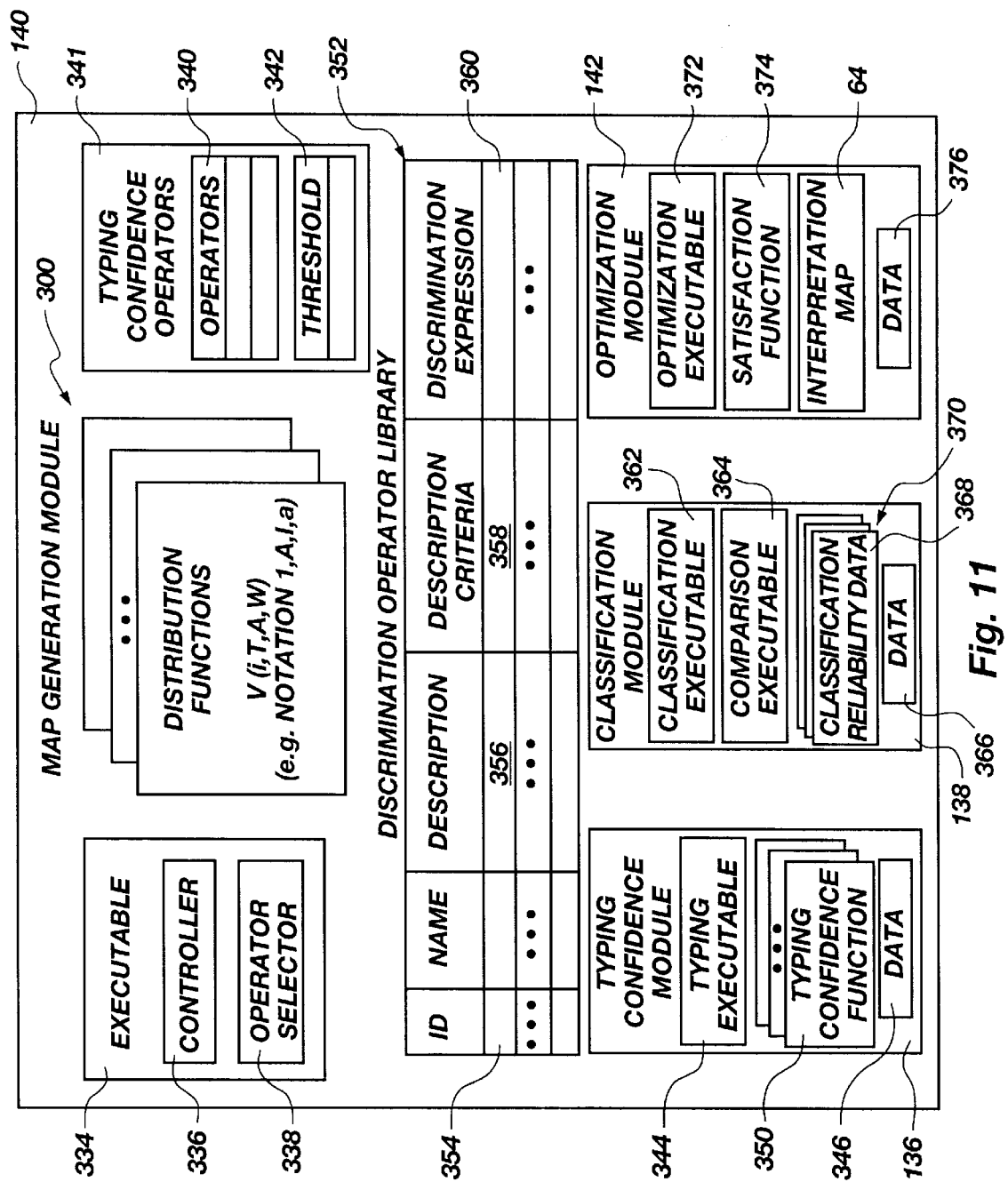
FIG. 11 is a schematic block diagram of one embodiment of a map generation module of FIG. 3.

Referring now to FIGS. 11–15, and more particularly to FIG. 11, a map generation module 140 may provide an interpretation map 64, by using the distribution functions 300. Each of the distribution functions represents a set or surface 320 of values (V) 294. Each value of the attribute value 294 corresponds to an instance (i), a type (T) 322 of an event 76, an aggregator or aggregation function (A) 290, and a weight table (W) 240. In the Figures, the four dimensional domain of i, T, A and W, may be presented by Arabic numerals, uppercase letters, Roman numerals and lower case letters, respectively.

The map generation module 140 may include an executable 334 or executable module. The executable 334 may include a controller 336 for managing the operation of various functions within the map generation module 140.

Likewise, an operator selector module 338 or operator selector 338 may provide for inputs by a user or other executable for selecting various inputs and methods. A selection operation may select a goal operator. A goal operator may be selected mathematically to correspond to any discrimination or interpretation basis that may be articulated. Selection of a goal operator is an arbitrary choice. A user (human operator or electronic processor) may select a goal for evaluation or may select a goal operator previously determined to provide a particularly beneficial result in a circumstance of interest.

Goal operators that may be selected may include, for example, maximization of the number of correct classifications of epochs as corresponding to an event type A, event type B, etc., maximize a sum of fractions of classification of epochs, such as assuring that the highest number of A's is in the class with A's and the highest number of B's is in the class with B's, maximization of correct classification of all elements of a single class of epochs, such as assuring that all A's positively identified, whether or not all B's are negatively improperly identified, maximization of confidence level, such as assuring with a high degree of confidence that any element identified as an A is certainly an A and not a spurious B improperly classified. Thus, an A and a B may describe separately identifiable event types, conditions, states, classes, interpretations, categories, or the like.

One may note that to maximize confidence is somewhat empathetically maximizing the number of correct values of a particular type. That is, in the former condition, one desires to be absolutely sure that one attribute value is not misclassified, as opposed to assuring that every possible potential member of a class of attribute values is included in a class. A user may select a goal based on previous experience, what is needed for the application at hand, or on some arbitrary choice. However, in a classification context, it may be possible that a user will have some knowledge indicating that particular inclusionary or exclusionary goal will best achieve the classification of attribute values into a useful subset.

In selecting a goal operator a user actually selects some type of classification operator that is calculated to optimize some discrimination goal distinguishing between two states A and B. The goal operator is indeed an operator that operates on the two distribution functions D (A) and D (B). The result of the operation of the goal operator G is a membership function or typing confidence function C (v) where C is a membership function or typing confidence function mapped between negative one and positive one, and V is a value corresponding to a distribution function of both the set or collection of A values and the set of B values. Thus, a membership function or a typing confidence function is the functional relationship output from the goal operator operating on the distribution of A's and the distribution of B's according to value. Thus, each value has a membership function that classifies it with a degree of certainty, probability, or membership in the class of A or the class of B.

A level, a degree, a presence, a certitude, a probability, a membership weight, or other similar terms may be used to express the concept of a membership value or typing confidence value that corresponds to some degree of certitude or inclusion according to the goal operator.

In fuzzy set theory, classification of phenomenon as members of classes of sets is done by degree or level, and is thus typically some number between zero and one, indicating a probability or possibility of membership. The number is not always probability, but may sometimes be interpreted as a probability or as a some normalized degree or level of membership of a particular object, element, value, or member in a particular set.

In an apparatus and method in accordance with the invention, a membership function may actually exist between two sets and not be found to only a single set. Thus, any value may have associated with it a fuzzy set pair, wherein a first element of the pair corresponds to a membership level, degree, confidence, or certitude corresponding to membership in event type, class, group, or set A, whereas a second element of the pair may represent the same value and its relationship to a set B. Of course, the decision could be a digital decision in which membership is assigned as a zero or a one or an A or a B. However, the method disclosed herein provides additional information beyond the digital decision of strictly crisp membership in A or B.

In general, a membership function or typing confidence function is not entirely independent of the optimal weight table, nor the aggregation functionals. Rather, the membership function is closely related thereto. Thus, a particular subset of weight tables may be particularly well adapted to distinguishing elements of class A from class B according to some criterion. For example, the expression "optimal" for weight tables has meaning in terms of the particular goal operator for which the membership function is to be optimized. Thus, "optimal" really only has meaning relative to a particular purpose.

The aggregation functionals represent several particular approaches to aggregation of information within a particular superposition segment or contrast segment into a single point. Thus, the attribute values each represent a single point corresponding to a single aggregation functional operating on a particular superposition segment or contrast segment which is itself a superposition of the data from several segments in the same epoch (several features of several channels during the same time period). Thus, when conducting a comparison between attribute values in state A or of event type A and attribute values of state B or of event type B, each value corresponds to multiple channels within a single epoch. However, multiple layers of epochs may exist in the comparison. Note that all the channels have been expanded, weighted, and superimposed to a single superposition segment or contrast segment which is mapped several different ways by several different aggregation functionals to create several corresponding attribute values which may then be bundled according to event type or state in a comparison. Notice that the goal operator operates to combine all the information from multiple epochs of two event types or a pair of event types into a single membership function or typing confidence function across all attribute values. However, the different aggregation functions used for creation of attribute values may have varying degrees of quality, accuracy, or certainty in the membership result for the same data.

Figure 13:
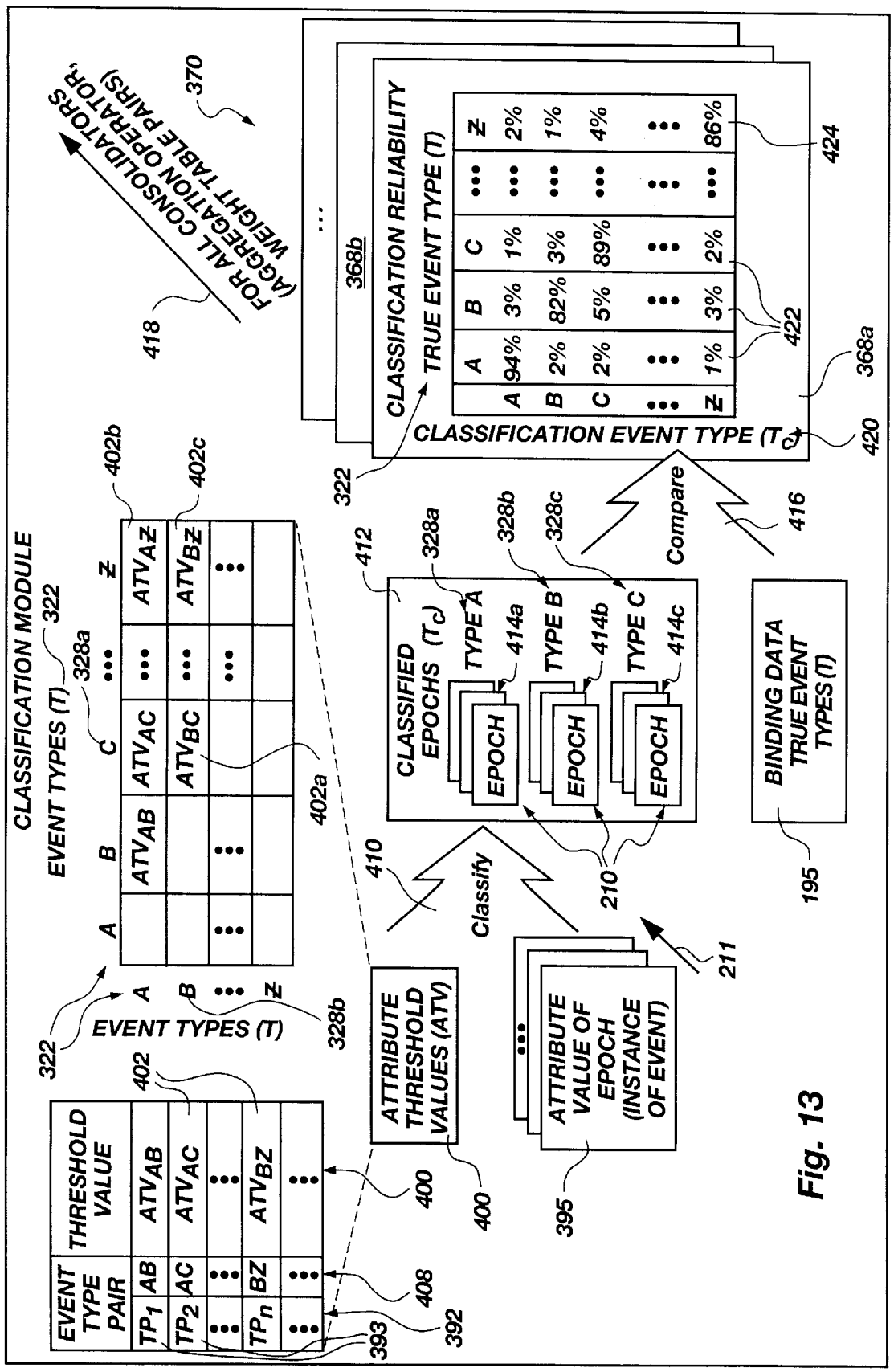
FIG. 13 is a schematic block diagram of a classification module consistent with FIG. 11.

In FIG. 13, the classifications and comparisons are based on attribute values corresponding to event type A and event type B for the same aggregation function and weight table. However, many event types, aggregation functions and weight tables are considered with their corresponding attribute values.

After building a membership function an additional step may be a traverse over all aggregation functions and weight tables. Accordingly, one may loop through each of the aggregation functions ($AF_1$, $AF_2$, $AF_3$, . . . $AF_K$) to capture each of the comparisons between the collections of attribute values $(AV_{1A})$ and $(AV_{1B})$, as well as $(AV_{2A})$ and $(AV_{2B})$, and so forth down to $(AV_{KA})$ compared to $(AV_{KB})$. Of course, different distributions will have different shapes and different distribution attribute values. Thus, one particular goal operator may actually provide a nearly perfect distinction between events from type A and type B by means of generating an optimal membership function or typing confidence function of attribute values. Aggregation functionals may exist in plenitude in order that a best aggregation function may be achieved.

(A particular aggregation functional may be selected in combination with a goal operator in order to optimize the precision of membership distinction for a particular value in a distribution function. Thus, given a set of candidate data corresponding to several epochs each having several channels of data and each epoch corresponding to one of two possible event types or states of which both states (A and B) are represented, a set of candidate weight tables, a set of candidate aggregation values (attribute values) and a set of membership functions and distribution functions exist. From this set of patterns (patterns of weights or weight tables), aggregation values (from aggregation functionals operating on superposition segments or contrast segments), distribution functions and membership classification functions or typing confidence functions, one may select an optimal subset of all the foregoing corresponding to a particular goal operator in order to provide maximum distinguishability between members of the two classes of events. In fact, membership functions may be ordered just as the distribution functions were ordered in terms of how well each achieves the discrimination of the goal operator. Thus, they may be ranked or ordered according to their ability to distinguish between membership in class A and class B (event type A and event type B).

Ordering may involve taking the very best one typing confidence function or membership classification function. Alternatively, the best few, the top half, or all weighted according to some ability to distinguish, may be used. One simple method for distinguishing the "goodness" or the "veracity" of a membership classification function is by running an additional set of data not previously used to create the system of weight tables, aggregation values, and membership functions. The classifications resulting from the new data may be compared using their known state memberships, labeled in the beginning, to determine the accuracy of the classification resulting from the exercise of the membership functions. Thus, according to some goal of confidence, lack of misses, lack of false negatives, or the like, the membership classification functions may be ranked and used according to how they achieve the desired goal.

The distribution functions 300 may be provided from the consolidation module 130. However, certain operators 340, may be characterized as typing confidence operators 341 to be used by a typing confidence module 136. Similarly, a threshold 342 or confidence threshold 342 may be provided, selected, or otherwise determined for evaluating outputs of the typing confidence module 136. In one embodiment, a set of thresholds 342 may be generated as outputs of the typing confidence module 136.

The typing confidence module 136 may include a typing executable 344. The typing confidence executable 344 may use data 346, including the distribution functions 300, and the typing confidence operators 341 to produce typing confidence functions 350.

Figure 12:
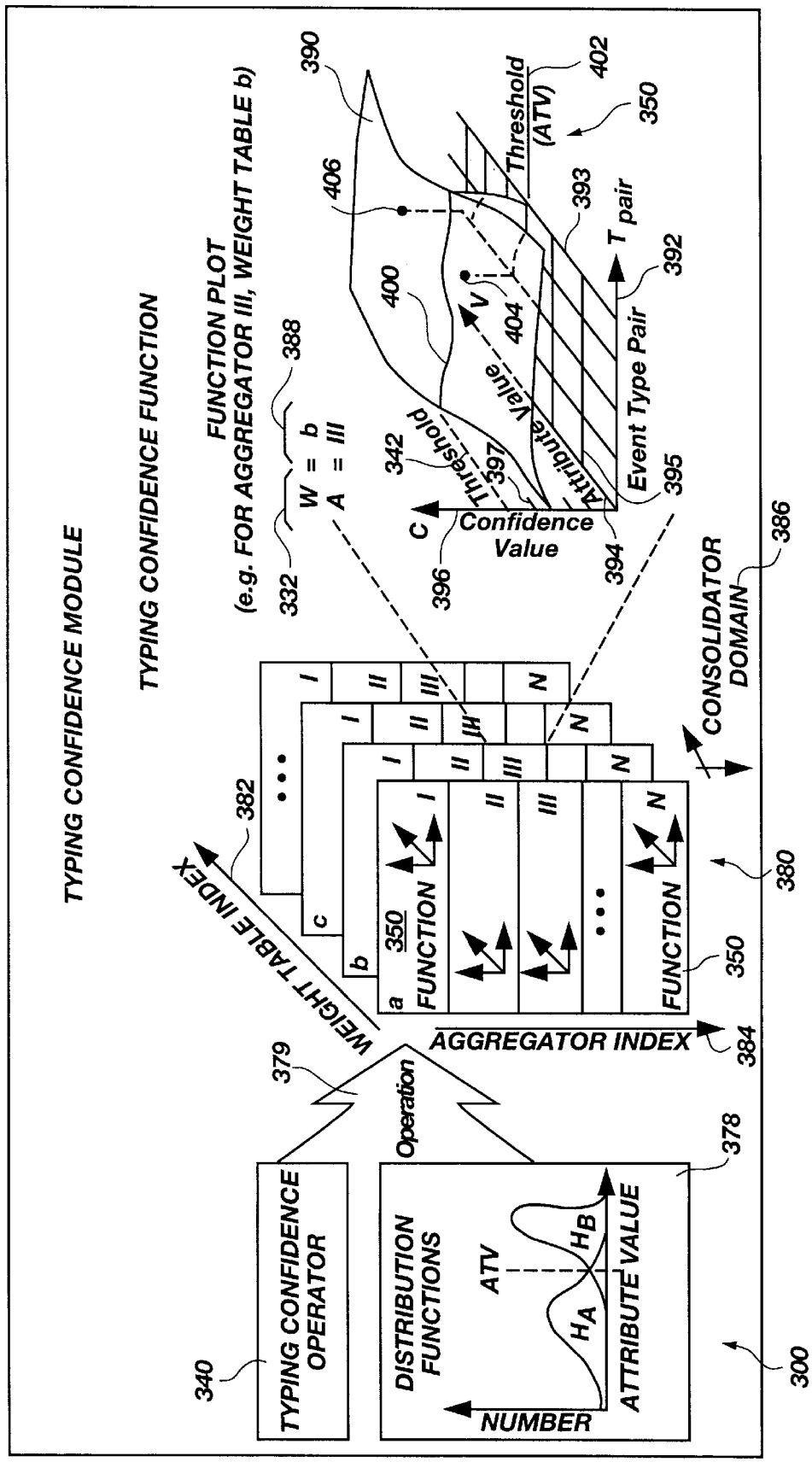
FIG. 12 is a schematic block diagram of one embodiment of a typing confidence module consistent with FIG. 11.

FIG. 12 illustrates in more detail the approach and significance of typing confidence functions 350 output by the typing confidence module 136. The data 346 may also include other supporting data for implementing the typing executable 344 to enable typing or classification of feature segments 228 by event type 104.

The typing confidence functions 350 in combination with selections from a discrimination operator library 352 may be used for purposes of classification. The discrimination operator library 352 may include identifiers 354 such as an ID or ID number, or name. Corresponding to each identifier 354 may be a description 356. The description 356 may aid a user in quickly determining the nature of a particular discrimination criterion 358 or discrimination expression 360. Discrimination criteria 358 and discrimination expressions 360 may be bound together under a single identifier 354. In an alternative embodiment, discrimination criteria 358 and discrimination expressions 360 may be individually located by separate identifiers 354. However, in one presently preferred embodiment of an apparatus and method in accordance with the invention, certain discrimination criteria 358 may apply particularly well to certain discrimination expressions 360 for defining selection of certain sets of event types 104, 322.

The classification module 138 may receive the typing confidence functions 350 from the typing confidence module 136. A classification executable 362 may use the typing confidence functions 350 along with the confidence thresholds 342 to determine an attribute threshold value 402. The attribute threshold value 402 may be used by the classification executable 362 in order to classify individual epochs 210 according to event type 104. A comparison executable 364 may use classification outputs from the classification executable 362 for providing classification reliability tables 368 or other representations of classification reliability 370.

The optimization module 142 may receive classification reliability data 370 as all or part of the data 376 used by an optimization executable 372. The optimization executable 372 provides satisfaction functions 374, and ultimately an interpretation map 64.

Continuing to refer to FIGS. 11–15, and particularly FIG. 12, a typing confidence module 136 may operate in one of several modes. For every event type 104, an occurrence of that event type 104 and the non-occurrence of that event type 104 may be treated as two separate events and event types. Thus, in general, every event type 104 may actually be categorized or discriminated against another event type 104 which is the non-occurrence of that same event type 104. A case of particular interest may also include different epochs 82, 210 that are of different event type 104. Accordingly, distinctions between two particular events (e.g., such as opposite directions of motion) may be considered mutually exclusive or otherwise distinguishable. Thus, a generalized method for distinguishing event types 104 from one another involves pairing of event types. In another embodiment, two epochs 82, 210 or event types 104 having no cognizable relationship to one another may also be paired. This type of pairing is useful for determining whether an underlying, non-obvious relationship exists between parameters corresponding to the respective epochs 82, 210 or event types 104. Particularly in biological organisms, the relationships between disparate epochs 82, 210 and event types 104 may not be well understood. Accordingly, one way to distinguish an epoch 82, 210 (and event type 104) from all other epochs 82, 210 (and event type 104) is to determine what that epoch 82, 210 (and event type 104) is not.

In one presently preferred embodiment of an apparatus and method in accordance with the invention, distribution functions 300 may be represented as histograms 378. The histograms 378 are also a particular type of distribution function 300, but simply represent certain information in another format.

A distribution function may be represented as a histogram. That is, a histogram may be viewed as an anti-integral of a standard distribution function. Accordingly, the abscissa on a histogram is the value in question while the ordinate (y axis) represents the number of the samples that exist at a particular value or between two nearby values. Accordingly, a histogram of all attribute values corresponding to event type A and event type B may represent two distribution curves (like a gaussian distribution, but need not be gaussian) in which some central portion may contain a majority of samples while the edges may contain lesser numbers.

The typing confidence operators 340, or simply operators 340, may operate on the distribution functions 300 in an operation 379 producing tables 380, or alternately referred to as confidence tables 380 or typing confidence tables 380. Each of the tables 380 may correspond to a weight table index 382 identifying a particular weight table 240 corresponding thereto. Within each table 380, an aggregator index 384 may indicate a particular aggregation function 290 or aggregation operator 290 (e.g., aggregation function 290, etc.) corresponding to a particular typing confidence function 350.

One may think of a weight table index 382 and an aggregator index 384 as defining a consolidator domain 386. Any point in a consolidator domain 386 corresponds to a particular weight table 240 from the weight table index 382, and an aggregator 290 from the aggregator index 384.

A consolidator 332 represents a point in the consolidator domain 386. For example, the consolidator pair 388 from the tables 380 corresponds to a consolidator domain 386 associated with a surface 390, or typing confidence function 390. The surface 390 represents values 390 over a domain defined by an event type pair $T_p$ 392 or type pair axis 392, and an attribute value axis 394. The attribute value axis 394 extends over all of the attribute values 294 along the attribute value axis 326 (see FIGS. 9–10). A particular value 395 along the attribute value axis 394 designates a particular, single attribute value. Similarly, a confidence value axis 396 represents values for the surface 390. Accordingly, a single value 397 or confidence value 397 along the confidence value axis 396 defines a plane normal to the confidence value axis 396.

In one embodiment of an apparatus and method in accordance with the invention, a threshold 342 or typing confidence threshold 342 may be provided in the map generation module 140. The threshold value 342 or threshold 342 is not necessary in some embodiments of the invention. Nevertheless, a threshold 342 may be selected, generated, or otherwise provided. In FIG. 12, the threshold 342 corresponds to a value 342 along the confidence value axis 396. Thus, the threshold 342 defines a plane normal to the confidence value axis 396, and substantially parallel to the domain plane defined by the event type pair axis 392 and the attribute value axis 394. One may note that the threshold 342 thus defines a function 400 or curve 400 defining attribute values 394 in the surface 390 at the threshold value 342.

Similarly, the function 400 traces along the surface 390 defining therebelow in the domain 392, 394 a threshold 402. The threshold 402 may be thought of as an attribute threshold value 402. The attribute threshold value 402 as it intersects the space defined by the event type pair 392 and the attribute value 394 axes, defined those attribute values 404 lying below the threshold 342 and "below" the threshold 402. Similarly described or defined are those attribute values 406 lying above the threshold 342 (confidence value threshold 342) and the threshold 402 (attribute threshold value 402). Thus, the surface 390 (typing confidence function surface 390) may map directly from a confidence value threshold 342 to an attribute threshold value 402 and vice versa.

The threshold 402 may arise in many circumstances from a distribution function 300, 378 directly. For example, histogram 378 provides one example of an attribute threshold value 402.

Referring now to FIG. 13, and generally to FIGS. 11–15, a classification module 138 may use, as inputs, attribute threshold values 400. Attribute threshold values 400 may be represented in a one-dimensional space, bound to event type pairs 392 identified as event type pairs 408. The event type pairs 392, of which specific instances 393 are illustrated, correspond to types identifying pairings 408 of particular event types 322 (see FIG. 10). Alternatively, event types 322 may be compared with other event types 322, resulting in attribute threshold values 402 (e.g., 402a, 402b, 402c) corresponding to each pairing 408 of types 322.

The attribute threshold values 400 may be used to compare each of the attribute values 294 in the distribution function 300 (surface 320) illustrated in FIG. 10. The attribute values 395 extend over all instances 324 of event types 322 of epochs 82, 210. Accordingly, the attribute values 395 correspond to individual epochs, extending across an epoch space 211 of all epochs 82, 210. Accordingly, a single attribute value corresponds to one epoch 82, 210.

A classify operation 410 or classify process 410 may be completed by the classification executable 362 to classify and divide each of the attribute values 395, providing groups of classified epochs 412. The groups 414 may each correspond to a particular event type 328 (e.g., 328a, 328b, 328c). Thus, each individual group 414 (e.g., 414a, 414b, 414c) contains some number of epochs 210 whose corresponding attribute value 395 has been distinguished according to some attribute threshold value 400.

It is important to remember that each attribute value 395 corresponding to an epoch 210 is a single value corresponding not only to one epoch 210, but also to a single consolidator 332. Thus, every consolidator 332 may give rise to another attribute value 395 for each epoch 210 to which it is applied.

A compare process 416 may compare binding data 195 (see FIG. 5) with the classified epochs 412, or groups 414 of epochs 210. The binding data 195 indicates the true type 322 corresponding to any particular epoch 210 and corresponding event type 104. Accordingly, the compare process 416 may operate over all consolidators 332 along some consolidator axis 418. The order of consolidators (pairs of aggregation operators and weight tables) may be somewhat arbitrary along the consolidator axis 418. Nevertheless, for each consolidator 332 along the consolidator axis 418, a classification reliability table 368 may be provided. For example, the classification reliability table 368a corresponds to a particular consolidator 332.

The classification reliability table 368a compares event types 420 as classified ($T_c$) 420 against true event types (T) 322. For each pair of classification event type 420 (classified type 420) and true event type 322 (type or true type 322), is a corresponding element 422. The element 422 is a reliability measure 422. The reliability measure 422 indicates by an appropriate measure, such as a percentage, for example, the number of true event types 322 that have been classified as various classification event types 420.

In one presently preferred embodiment, a reliability measure 424 along the diagonal of the classification reliability table 368 (e.g., 368a) may indicate the percentage of events 210 that have been properly classified with a classification event type 420 the same as the true event type 322 obtained from the binding data 195. The reliability measure 424 along the diagonal of the table 368a should, in one presently preferred embodiment, be as high as possible. A high percentage 424 indicates that most of the true event types 322 are being properly classified. Reliability measures 422 that are high and distant from the diagonal measure 424 (off-diagonal reliability measures 422) indicate confusion with the true event type 322 during classification operations 410. Strong diagonal values 424 with low off-diagonal values 422 indicate that a particular consolidator 332 and corresponding typing confidence function 350 form an excellent discriminator for identifying a particular event type 322. Additional tables 368b correspond to other consolidators 332 along the consolidator axis 418.

In general, a classification reliability table 368 indicates, with the values 422, 424 much about the correlation between particular event types 322, anti-correlation between true event types 322, and lack of relationship therebetween. Thus, the classification reliability tables 368 may be used to identify and analyze disjoint sets, conjoint sets, subsets, proper subsets, and the like of particular combinations (sets) of event types 322.

In one present preferred embodiment, a consolidator 332 may be selected by a user or other executable to be applied to events 76 grouped by some observable relationship. Thus, a consolidator 332 may be very useful for distinguishing a particular event 76 from an opposite 76. For example, a single consolidator 332 might not be expected to distinguish every event type 322 from every other event type 322. Nevertheless, a particular pair such as an event type A and event type B may be easily distinguished from one another, and reliably so by a particular consolidator 332. Meanwhile, the same consolidator may not give the same reliability in distinguishing between some other event types 322 such as event type C from an event type D.

Figure 14:
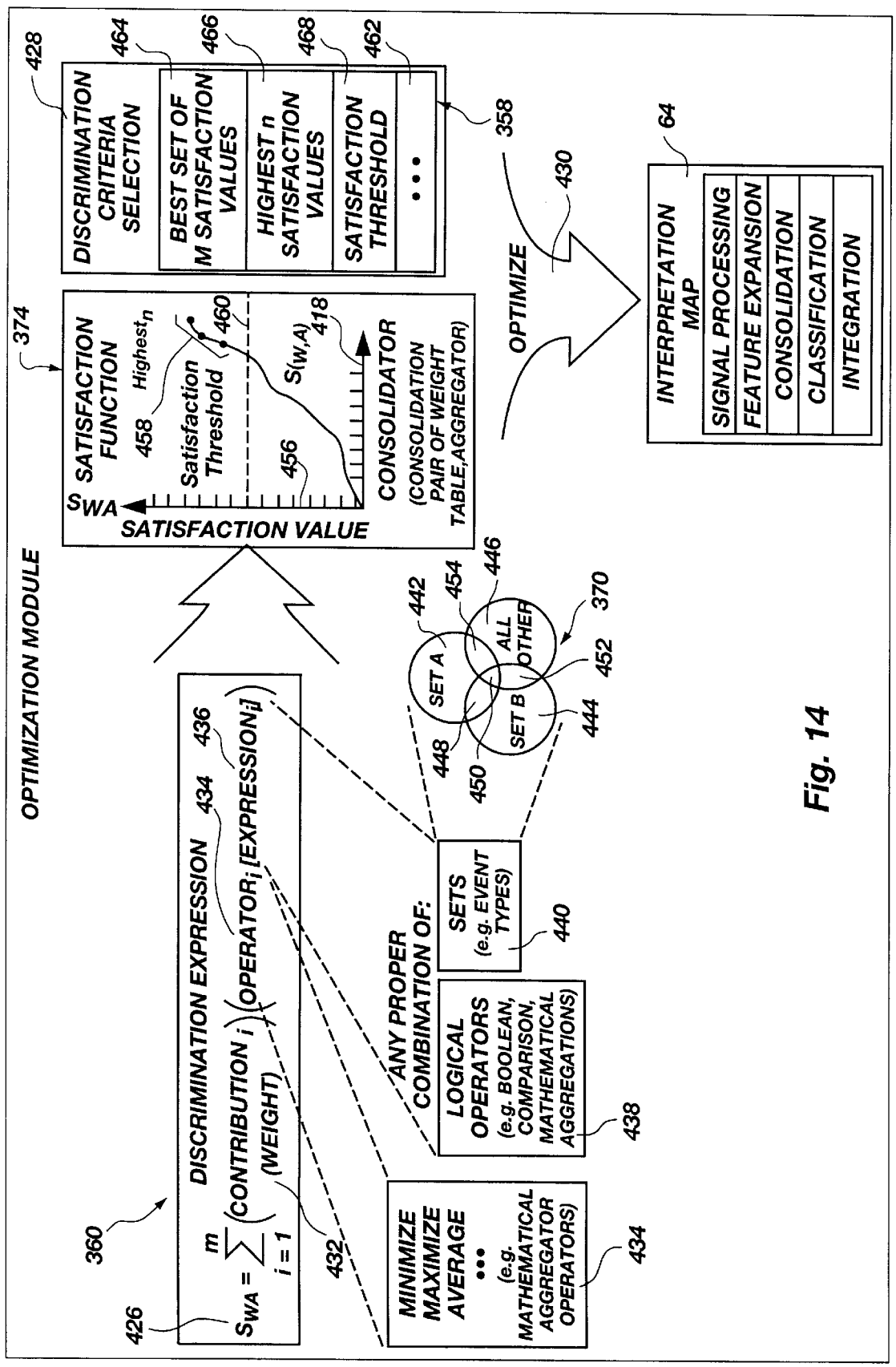
FIG. 14 is a schematic block diagram of a optimization module consistent with FIG. 11.

Referring now to FIG. 14, and generally to FIGS. 11–15, an optimization module 142 may provide satisfaction functions 374 and interpretation maps 64. A discrimination expression 360 may be available from the discrimination operator library 352. A discrimination expression 360 may output a value of a satisfaction function 426. The discrimination expression 360 may output satisfaction functions 374 to be compared with discrimination criteria 358 selected in a discrimination criteria selection 428 or selection module 428. An optimize 430 or optimization process 430 may combine the information from the satisfaction function 374 and discrimination criteria selection 428 to provide the interpretation map 64.

Considering the discrimination expression 360, a summation of individual elements may be made. Each element may include a contribution weight indicating the contribution of effect that a particular element (element i) will be allowed to contribute to the satisfaction function 426. Each element may include an operator 434. The operator may thought of as a minimum, maximum, average, or other mathematical aggregator operator. The aggregator operators 434 are not to be confused with the aggregation operators 290.

Nevertheless, the aggregators 434 may be selected from the same classes of mathematical operators 434 as the aggregator operators 290. However, it is simplest to visualize, and most practical in one presently preferred embodiment, to use an operator such as a maximize operator 434 for maximizing or minimizing a value of the expression 436. For example, in optimization theory, maximization or minimization of some expression or cost function is one preferred method for determining a minimum or maximum of the cost function. The cost function or expression 436 may be thought of as characterizing some relationship or value that is to be maximized or minimized appropriately.

The expression 436, may thus be constructed to maximize or minimize a percentage of events 76 and their corresponding epochs 82, 210 correctly classified in some particular set. In general, the expression 436 may include any proper combination of logical operators 438 operating on sets 440 The sets 440 are one presently preferred representation of the classification reliability data 370.

For example, a set A 442 may correspond to a particular event type 322. The set A 442 may contain all of the those events 210 that have been classified as being of the type 322 corresponding to the set A 442. Similarly, a set B 444 may correspond to a different type 322. A set 446 may characterize yet another event type 322 or some combination of event types 322. For example, all events not of one particular type or two particular types may be equally useless or misclassified (confused with, not distinguished from) events from set A, set B, or another set. Thus, the set 446 may include another or all other sets that are not of a type of interest of a type 332 in the set 442 of interest.

One may note that the set 448 may contain a representation for epochs 210, events 76, and event types 420 that have been classified as both pertaining to set A 442 and set B 444. Similarly, the set 450 represents all epochs 210 and events 76 that have been classified as both pertaining to set A 442, set B 444, and the other set 446. The sets 454, 452 correspond, respectively, to epochs 210 and events 76 that are classified in both set A 442 and other sets, and set B 444 and other sets 446, respectively.

Thus, in the example of FIG. 14, the logical operators 438 may be used in virtually any appropriate (mathematically proper, and interesting to a user) combination with any of the sets 440. Thus, an operator 434 may, for example, seek to maximize an expression 436 that maximizes membership in set A 442, while minimizing membership in sets 448, 450, and 454. In another example, one may seek to maximize membership in the set 442 (set A), maximize the membership in set B 444, while minimizing the contents of the sets 448, 450. Thus, set A 442 and set B 444 may be identified while confusion between the two sets 442, 444 may be minimized.

Note that the contribution weight 432 may be used to make a requirement of an operator 434 strong or weak. For example, one may determine that the set 450 is to be minimized by an operator 434, but is not particularly important, only desirable. Accordingly, such an operator 434 in corresponding expression 436 may be given a modest value of a contribution weight 432, compared to a contribution weight 432 of much greater value for some other set.

The satisfaction function 426 may be provided over a consolidator domain 418 or consolidator axis 418. Thus, for any consolidator value 418, a satisfaction value 426 may be measured along a satisfaction value axis 456. The highest number 458 of satisfaction values 426 may be found across the entire consolidator space 418 or consolidator axis 418. In one embodiment, a value of a satisfaction threshold 460 may be established, to identify those satisfaction values 426 that are acceptable, and those that are not.

An optimize 430 or optimization process 430 may use discrimination criteria 358 selected by a user, automatically, or otherwise provided to evaluate the satisfaction function 374. The discrimination criteria 358 may include a single criterion 462 or several criteria 358.

For example, the criterion 464 may cause the optimization process 430 to select a best set of m satisfaction values 426. The criterion 464 may not define the number m. Rather, some satisfaction threshold 460 may be established, and all satisfaction values 426 exceeding the threshold 460 may qualify as members of the best set of m satisfaction values. The criterion 464 implies that some basis for determining "best" satisfaction values 426 is provided, with all satisfactory results being reported.

In anther example, a criterion 466 may request the highest n satisfaction values 426. The other number n may be defined. Thus, the top one, two, three, or other number, of satisfaction values 426 may be reported. The criterion 466 is particularly useful when a relatively large number of events 76 and epochs 210 is available. For small sample sizes, experience indicates that a user may be best served by considering only the best satisfaction value only, rather than give an inordinate significance to other consolidators 332 that may inappropriately tune the interpretation map 64 to small, random, fluctuations within the small sample set of events 76 and epochs 210. For very large sample sets, a large n may be useful, since the probability favors several consolidators 332 being appropriate, particularly in combination in order to maximize a signal to noise ratio for the interpretation map 64.

A criterion 468 may provide an output including all satisfaction values 426 above a satisfaction threshold 460. In this case, the satisfaction threshold 460 may correspond directly to a relatively small subset of consolidators 332 along the consolidator axis 418. These satisfaction values 426 exceeding the threshold 460 may be thought of as peaks along a mountain range that are all the satisfaction values 426 distributed along the consolidator axis 418. In the satisfaction function 374 illustrated in FIG. 14, all satisfaction values 426 have been ordered from minimum to maximum along the consolidator axis 418, to provide a monotonic function with a single peak.

In one embodiment, the satisfaction threshold criterion 468 may be the basis for the criterion 468 selecting the best set of m satisfaction values 426. However, some other basis may be provided for the criterion 464. For example, a user may determine that certain consolidators 332 are more efficiently processed, and therefore provide a more rapid processing of the classification system 66. Variations, standard deviations from a norm, and the natural trade-offs between speed and accuracy in general, may all be considerations for the criterion 464. Likewise, trade-offs may be exercised for the speed and accuracy of the learning system 62 as well as the speed and accuracy of the classification system 66. For example, in certain applications, learning may take a long period of time, but classification must be relatively instantaneous. Accordingly, a basis for the criterion 464 may be an accuracy optimization of the learning system 62 with a speed optimization of the classification system 66.

The optimizer 430 or optimization process 430 may be thought of as applying the discrimination criteria 358 to the satisfaction function 374. A result of the optimization process 430 is identification of a number of selected consolidators 332 that may or should be included in the interpretation map 64 to enable the classification system 66 to provide discrimination between various event types 104, 322. The interpretation map 64 includes several elements 470 (see FIG. 15) representing optimal parameters, functions, and operators for executing the method 121.

The interpretation map 64 may be thought of as a collection of parameters, operators, functions, and the like for executing the process 121 to implement the classification system 66. That is, the process 121 implements in the modules 120, the learning system 62 of FIG. 2. Likewise, the process 122, with the same modules 120, implements the classification system 66. As discussed, a difference between the learning system 62, and the classification system 66 is the learning data 68 compared to verification data 71 or non-associated data 72. Likewise, the feature expansion module 126, weight table module 128, and consolidation module 130 may use candidate parameters to implement a learning system 62, and optimized parameters (from the interpretation map 64) for implementing the classification system 66.

Figure 15:
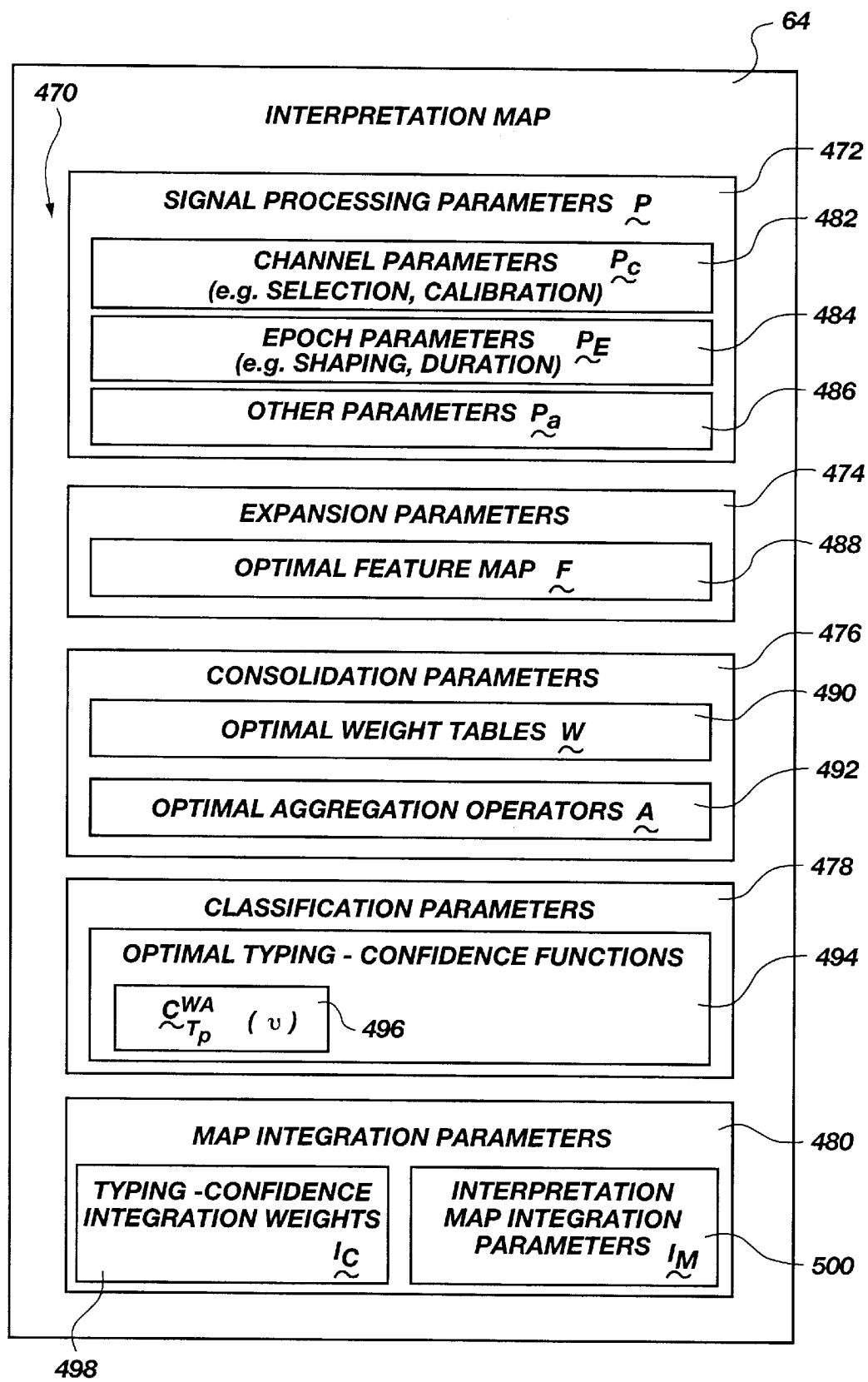
FIG. 15 is a schematic block diagram of one embodiment of an interpretation map consistent with FIG. 2, and FIG. 14.

Referring now to FIG. 15, and to FIGS. 11–15, generally, an interpretation map 64 implements, represents, encodes, and is comprised of the specific knowledge gained from the learning system 62. Accordingly, the optimization process 430 has enabled selection of optimal signal processing parameters 472, optimal expansion parameters 474, optimal consolidation parameters 476, optimal classification parameters 478, and optimal map integration parameters 480.

The signal processing parameters 472 may include, for example, channel parameters 482. The channel parameters may include the selection of a particular sensor, a particular set of sensors, a particular attribute of a signal (e.g., frequency, mean, maximum, etc.) as well as calibration data that might be appropriate for an original signal sensor.

Likewise, epoch parameters 484 may include a length, shape, time duration, latency, latency between channels, latency of a channel 84 with respect to an event 76 or the like. Other signal processing parameters 486 may be appropriate for a particular system, a particular subject, application, and so forth.

Expansion parameters 474 may include an optimal feature map 488. The optimal feature map may include the feature operators 230 deemed by the optimization process 430 to produce the best feature maps 222, 200. Part of a feature map 200 is the domain made up of the variable X 224 and variable Y 226. Thus, a feature map 200 is defined in terms of the feature operators 230 and the domain variables 224, 226, which may be selected, as described above, from frequencies, times, time lags, phases, and the like.

Consolidation parameters 476 may include optimal weight tables 490 and optimal aggregation operators 492. The optimal weight tables 490 may be selected by the optimization process 430 from the weight tables 240 created by the weight table module 128. Likewise, the optimal aggregation operators 492 may be selected from among the aggregator operators 290 provided by the aggregation module 134 of the consolidation module 130. Note that the optimal weight tables 490 and optimal aggregation operators 492 may be bound to define a consolidator space 418, described above.

The classification parameters 478 may include optimal distribution functions and optimal typing-confidence functions 494, 496. For example, the confidence function 496 may be selected from the typing confidence function 350, particularly the surface 390. Accordingly, the optimal typing-confidence function 496 may typically be bound directly to a consolidator (WA) corresponding to an optimal weight table 490 and a optimal aggregation operator 492. Similarly, the function 496 my also be associated with a particular type pair ($T_p$) 393 selected from the event type pair axis 392 or set 392. FIGS. 12 and 13 illustrate type pairs 392 and specific type pairs 393, that may correspond to the optimal typing-confidence function 496. Referring to FIG. 12, one may note that a particular type pair 393 corresponds to a curve of intersection between a plane normal to the event type pair axis 392 and intersecting the typing confidence function surface 390.

The map integration parameters 480 may include both typing confidence integration weights 498, as well as interpretation map integration parameters 500. The typing confidence integration weighs may correspond to weights or contribution fractions that will be assigned to a particular optimal weight table 490 and optimal aggregator 492. These contribution fractions or weights may provide for use of multiple optimal weight tables 490 and multiple optimal aggregation operators 492, while weighing the relative contributions of each consolidator pair 490, 492. For example, the typing confidence integration weights 498 may include weighing functions or weighing parameters for aggregating multiple optimal typing-confidence functions 496.

In one embodiment of an apparatus and method in accordance with the invention, a particular optimal typing-confidence function 496 may be evaluated at a particular attribute value 395 along an attribute value axis 394 (see FIG. 12), providing a specific typing confidence value. Thus, a parameter included in the typing confidence integration weights 498 may include a weight corresponding to certain values of the optimal typing-confidence function 496. Thus, for example, the function 496 may be evaluated at a particular value (V) 395. In one embodiment, satisfaction values 426 may be used like votes or weights. Accordingly, a particular optimal weight table 490, optimal aggregation operator 492, and optimal typing-confidence function 496 may be used in combination with one or more other optimal weight tables 490, optimal aggregation operators 492, and optimal typing-confidence functions 496. A contribution or weight of each such set may be based on the relative values of the satisfaction values 426, associated with each such set. The votes, corresponding to satisfaction values 426 may be normalized over the total number of votes to maintain a bound on actual numerical values of weighing functions. Thus, all votes may total a contribution of 100% for all sets included.

The interpretation map integration parameters, 500, or interpretation parameters 500 provides for weighing multiple interpretation maps 64. For example, in application, many movements may be interrelated, may be correlated, or anti-correlated. For example, movement of one finger of a hand may be done in coordination with movement of another finger of a hand for a total integrated motion. Thus, such complex motions that must be integrated together may require multiple interpretation maps 64 to be combined to represent a complex motion of several subordinate motions. Accordingly, a master interpretation map 64 may be combined from several other interpretation maps 64. Thus, similar to the typing confidence integration weights 498, the interpretation map integration parameters 500 may form weights to be applied to particular interpretation maps 64 to be combined. Thus, a master interpretation map 64, may actually contain a summation of weighted values of elements 470 from a plurality of interpretation maps 64.

For example, individual epochs 76 have associated time segments 69. A time segment has a length inherent in it. However, in different instances, an event 76 may occur rapidly, slowly, over a long time segment 69, or over a short time segment 69. Accordingly, correlations may require that a single event 76 be integrated, or analyzed over several different time segments 69. The interpretation map 64 resulting from each such individual instance of an event type 104 characterizing a particular event 76, may be represented by a master interpretation map 64. The master interpretation map 64 may include the contributions of various interpretation maps 64 weighted to achieve maximum precision over all anticipated time segments 69 (epochs 76). One may think of the time segments 69 as a duration corresponding to a particular epoch 76.

In another embodiment of an apparatus and method in accordance with the invention, the interpretation map integration parameters 500 may include weighing factors to be used in combining interpretation maps 64 generated based on different sensors, different types of sensors, and the like. For example, just as a particular channel 84 may provide certain data, the channel may be characterized by a particular sensor generating the signal data 80, and may be characterized by the type of data. Types of data may include electromagnetic, electrical, mechanical, sonic, vibration, sound, and the like, discussed above. Accordingly, a particular interpretation map 64, such as a master interpretation map 64, may include weighted contributions of the elements 470 of several interpretation maps 64 based on different sensor types. The interpretation maps 64 corresponding from different sensor spectra (e.g., light, sound, electromagnetic, electrical, etc.) may be combined according to weights included in an interpretation map integration parameter set 500.

From the above discussion, it will be appreciated that the present invention provides a novel apparatus and methods for signal processing, pattern recognition and data interpretation. The present invention also finds attributes of a signal that may be correlated with an event associated with the same time segment as the signal where a correlation is found by manipulating the signal data with various operators and weights to "expand the signal" into many different features.

It will also be appreciated that the present invention may process each signal piece or segment occurring over a time segment to determine a correlation between a known event and a particular, processed "feature segment." One presently preferred embodiment of the present invention also determines optimal ways to manipulate a signal for purposes of distinguishing an event from the signal.

A signal interpretation engine further may learn from at least two patterns or two event types derived from data collected from a series of related chronological events. Moreover, the present invention may analyze complex data, from whatever source, and classify and interpret the data.

The present invention will now be illustrated by reference to the following examples which set forth particularly advantageous embodiments. However, it should be noted that these embodiments are illustrative and are not to be construed as restricting the invention in any way.

EXAMPLE 1

Video Game Control via Brainwave Mind State Interpretation

For controlling games and other software programs by means of mind state interpretation the signal interpretation engine can be used to recognize and interpret the tiny cognitive signatures or patterns present in noisy brainwave signal data. The following steps should be taken to use a signal interpretation engine for this purpose.

Step 1: Game or software events of interest are time stamped (which involves placing clock time labels on the events of interest) and also every brainwave data point is also time stamped. There are two associations which need to be made. (1) Mind events (states of mind or cognitive conditions) need to be associated with software events such as, for example, game conditions, projected action conditions, key presses, mouse movements, screen shots, sounds, and others. For example, from the projected location of the ball in the software game of ping-pong (whether it is coming down on the right or left side of the screen) one can infer whether the attentive human player intends for the paddle to move to the right (mind-state of "intend paddle move to the right") or the left (mind-state of "intend paddle move to the left"). (2) Brainwave signal data needs to be associated with mind events (a function accomplished by the labeler or binding module).

Mind events can be time-stamped and placed in a mind-event list (or file). The wave packet (data segment) labeler or binding module can then cut out and shape those brain wave packets or data segments which were simultaneous with the particular mind events of interest. These brain wave packets or data segments will then all contain tiny patterns or signatures corresponding to the same mind event.

Step 2: Two labeled files (two lists of examples of signal data corresponding to the same two mind events) are then presented to the map creator (learning algorithm). The learning algorithm creates a map which is a mathematical construction encoding contrasting features of the two types of brain wave packets or data segments which are the most important features for correctly deciding to which of the two categories the packet belongs. The map contains the instructions on how to mathematically transform the contents of each wave packet or epoch segment into a mind-state activation, a mind-state probability, and/or a mind-state classification.

Step 3. The maps created by the learning algorithm can now be used to classify future brain wave packets which the learning algorithm has never before seen. The classification algorithm can use a map to interpret or infer the mind state present or contained in a particular brain wave packet. The parser can be used to prepare a real-time stream of wave packets of the same temporal length and shape. This parsed sequence of prepared wave packets can be presented to the classifier (classification algorithm) which will classify each wave packet into one of two distinct categories. The classifier also generates a real-time stream of mind-state probabilities and/or interpretations which indicates the degree to which the mind is in one state or in another.

Step 4. The mind-state probability stream can now be used to drive software events such as generate mouse movements, move ping-pong paddles, press keys and buttons, move cursors, or other events. For example, the mind-state probability stream can be translated into the location of a paddle at the bottom of a ping-pong game screen. For example, probability less than 0.2 could move the paddle to the left, probability greater than 0.8 could move the paddle to the right, and probabilities in between 0.2 and 0.8 could be used to place the paddle in the middle of the screen.

Step 5. New maps are periodically created and used in place of the old ones. In this way the maps can follow changes in neurophysiology allowing the map software and neurological connection patterns to evolve together to create increasingly accurate and more useful maps. In order to optimize interpretation capability and game control accuracy, a distinct and separate map should be created for each and every pair of mind states that need to be contrasted. For example one map is needed to discriminate intention to move LEFT versus intention to move RIGHT, another distinct map is needed to discriminate intention to move UP versus intention to move DOWN. As larger numbers of accurate maps are simultaneously employed to contrast different pairs of mind states, it should be possible to establish more and more control capability, accuracy, and variety.

EXAMPLE 2

Cancer Biofeedback Machine

Maps are used to help make cancerous tumors shrink and disappear by using tumor growth or decay measurements to label brainwaves, bodywaves or signals from the body, endocrine levels, behavior, environment, and stimulants such as drugs, diet, radiation, surgery, and exercise. The collection of multiple signal represented by brainwaves, bodywaves, endocrine levels, behavior, environment, stimulants, and other related entities area the "set of possibly correlating signal". This set of possibly correlating signal can be used in conjunction with a signal interpretation engine to aid in the therapy and cure of cancer. This can be accomplished by taking the following steps.

Step 1. Microchip sensors can be implanted inside a tumor or tumors or nearby them to detect changes in growth rate of the cancerous tissue by measuring temperature, chemical concentration potentials, electrical activity, and other physiological, physical, and chemical measures of tissue growth and change. Microchip stimulators can also be implanted in or near the tumors in order to stimulate tumor decay and shrinkage.

Step 2. These implanted sensors and stimulators can communicate with the outside world by means of microwave or radio frequency transmissions. This wireless communication capability will allow the sensors and stimulators to communicate with computer software running in real-time.

Step 3. The implanted sensors will deliver to the Cancer Biofeedback Software Program a multiple signal data stream corresponding to the types of physiological, physical, and chemical measurements of the tumor(s) that sensors are designed to measure. Growth events (times when the tumors are growing) and decay events (times when the tumors are shrinking) can be used to label wave packets from the "set of possibly correlating signal" as defined above.

Step 4. These labeled wave packets from the "set of possibly correlating signal" are fed into the map creator (the learning system) to create maps which discriminate between tumor growth and tumor decay. The efficacy and value of the constructed maps will depend on the degree to which tumor-growth or tumor-decay signatures are present in the various components of the "set of possibly correlating signal". The constructed maps will be unique and sensitive to the particular physiology of the individual for whom they are created. It seems likely that at least some contrasting signatures will be found and encoded within the cancer growth/decay maps for many if not all people. By carefully evaluating the constructed maps, physicians and patients will be able to determine which components of the "set of possibly correlating signal" are most instrumental and important (in other words which components correlate the most) for determining tumor growth and/or tumor decay.

Step 5. The growth/decay maps are used by the classifier (classification system) to create a tumor growth/decay probability stream from the "set of possibly correlating signal". The derived tumor growth/decay probability stream are used to drive video games and other biofeedback computer displays to help the patient choose, set, or "relax" into those healthy mind, body, drug, and other states which are most conducive to tumor decay and to stay away from those states which correlate with tumor growth.

Step 6. Stimulation sequences are also be employed to stimulate the cancerous tissues followed by sensor measurements to determine efficacy in tumor size reduction.

Step 7. While the tumor sensors are in place, direct measurements from the tumors are used to drive biofeedback displays according to traditional methods of biofeedback. After the tumor sensors are removed, the constructed maps are used in conjunction with the "set of possibly contrasting signal" to continue the biofeedback therapy.

Step 8. New maps are constructed on a periodic basis to increase accuracy and track any changes in the progression of the cure so as to always be using the currently most effective maps for a given therapy goal. The contrasting elements of a therapy goal (for example, tumor growth versus tumor decay) are the labels for the wave packet examples which are used by the learning algorithm to create a map.

EXAMPLE 3

Stock Market Prediction Machine

The signal interpretation engine is used to predict whether a particular stock price will go up or down during a future period if predictive patterns exist within the collection of available signal such as stock prices, mutual fund prices, exchange rates, internet traffic, etc. The signal interpretation engine makes good predictions even if these patterns are distributed across multiple signal and through complex signatures in time and frequency. In order to predict whether a particular stock price will go up or down or predict some other future activity of a market measure, the following steps should be taken:

Step 1. Market historical data is used to create two prediction event lists for the two market features that are to be predicted. The two prediction event lists are made by first deciding which market feature is to be predicted, how far into the future it is to be predicted, and how much historical data is to be analyzed to make the prediction. For example, if we decide to try to predict whether IBM stock prices will be higher or lower (by some significant amount) one week into the future by considering the history of fifty stocks and exchange rates over the previous two months, we create two prediction event lists as follows:

Step 1: The IBM-UP list is a list of two month periods for which IBM stock went UP (by some significant amount) one week into the future (from the price it had on the last day of the two month "wave packet" period). The IBM-DOWN list is a corresponding list for when IBM stock goes DOWN (by some significant amount) one week into the future.

Step 2. The two prediction event lists (IBM-UP and IBM-DOWN) are used with the labeler to cut out and shape those two month wave packets from the multiple signal of the fifty selected stock. (For example, the multiple signal can consist of the daily closing price for the fifty selected stocks and exchange rates.)

Step 3. The IBM-UP wave packets and the IBM-DOWN wave packets (as separate and distinct prediction-event examples) are fed into the map creator (learning algorithm) to create an intelligent map designed and tuned to discriminate between IBM-UP and IBM-DOWN wave packets.

Step 4. The efficacy and value of the constructed map is tested by using the classification algorithm (classifier) with the map to classify other historical stock market data (wave packets cut and shaped by the parser) which the learning algorithm has never before seen. If the classifier (using the map) can accurately predict a significant fraction of the IBM-UP and IBM-DOWN events then the map is likely to be useful and valuable as a one-week market predictor of the increase or decrease in the price of IBM stock. The more market measures considered, and the more wave packets examples presented to the learning algorithm, the better are the chances of constructing a map that is truly useful and valuable for prediction purposes. The more test data (wave packets) that are classified for testing purposes the better the chances of understanding correctly the true value, capability, accuracy, and potential of the constructed map.

Step 5. The map is used with the classifier to predict (classify into the one-week future IBM stock movement states of IBM-UP and IBM-DOWN) new wave packets prepared by the parser from the multiple times series of multiple market measures. In this way the map can be used as a market predictor.

Step 6. Periodically new maps are constructed to improve accuracy and follow possibly changing predictive patterns within the multiple market measure signal.

Step 7. Other different maps are constructed to predicted different features of IBM stock for different periods into the future (other than one week), using different collections of market measures (other than the fifty measures used in the above example), and by analyzing wave packets of different lengths (other than two months). Maps to predict features of other stocks (other than IBM) and other market measures (for example exchange rates or internet traffic) are then constructed.

Step 8. The different constructed maps are carefully tested and evaluated to decide which are the most predictive, accurate, and reliable.

Step 9. The weights in the maps are analyzed to see which features of which market measures are the most important for particular predictive purposes and thereby gain additional useful understanding of market mechanisms. This understanding is used to further improve the accuracy of future maps that are constructed.

EXAMPLE 4

Spinal Cord Reconnection Machine

The signal interpretation engine is of significant use in the creation of "software spinal cord bridges" and in stimulating the growth and reconnection of spinal cord neural tissues. This is done by capitalizing on the signal interpretation engine's ability to identify, recognize and interpret subtle patterns of neural and muscular activity. A software spinal cord bridge or spinal cord reconnection machine is constructed as follows:

Step 1. Microchip or other electric sensors and stimulators are first placed on the surface of the patient's body (periphery, hands, arms, legs, feet, etc.), on the head (EEG sensors), and implanted within the body both above and below the spinal cord lesion or region of spinal cord damage at the basal ganglia and (if possible without damaging tissue) within the spinal cord itself. The sensors and stimulators should be tiny and numerous. Care should be taken to minimize detrimental effects so as to not further damage any neural tissues. These sensors on the periphery, head, and in the ganglia and spinal cord measure electric potential and transmit this multiple (one or more signal of measurements for each sensor) signal information wirelessly (via microwave or radio frequency transmission) to a nearby computer for processing.

Step 2. A biofeedback computer display is set up to display signals coming from the sensors to the spinal cord patient in such a way as to motivate and encourage him or her to try to move his or her fingers and toes. The patient should be kept engaged in making the effort to move and control his limbs while the software creates event lists from activity sensors in the upper spinal cord region (above the lesion) that are measuring the patterns that correspond to intentional motor activations.

Step 3. The time-stamped motor sensor (spinal cord above the lesion) patterns are used to label the time-stamped brain wave packets (from sensors over the motor cerebral cortex).

Step 4. The time-stamped peripheral muscle electrical signals and touch (somatosensory) signals at the periphery are used to label the neural patterns induced (by stimulation) at the spinal cord below the lesion.

Step 5. The labeled wave packet segments should be used by the learning algorithm to create maps which can be used to create spinal-cord reconnection maps by associating intention to move with the motor neural patterns at the spinal cord which will induce the desired movements. Somatosensation spinal-cord reconnection maps are made in a similar way.

Step 6. The classifier is used with the motor maps and the somatosensation maps to help the patient regain control of and sensation from his limbs.

Step 7. The maps are periodically updated to account for new learning the neural pathways within the brain and spinal cord. In this way the patient is able to continually improve his or her bodily control and sensation.

Step 8. It is possible that this type of reconnection-learning when combined with injections of fetal brain tissue into the damaged spinal-cord lesion area will act to stimulate beneficial reconnections within the spinal cord and adjacent dorsal root ganglia. In this way it may be possible to completely or nearly completely restore function to handicapped individuals who now suffer paralysis due to spinal-cord injuries, or loss of function due to brain cell death, for example with cerebral palsy.

EXAMPLE 5

Multiple Sclerosis Biofeedback Machine

For treating neurological diseases such as multiple sclerosis the following types of steps are taken:

Step 1. Sensors are used to measure the growth and decay of myelin cells and myelinated tissues.

Step 2. Brainwaves and various other bodywaves are labeled by myelin growth/decay rates Step 3. The myelin-labeled wave segments in the learning system are used to produce myelin-growth interpretation maps.

Step 4. The myelin-growth interpretation maps with the classification system are used to drive and control video games.

Step 5. The video game-flow is structured such that the player is able to make progress toward the game objective when he or she generates brainwaves and/or bodywaves which are associated with myelin growth and not with myelin decay.

Step 6. The learning system is used to make new interpretation maps as needed to improve the therapy.

EXAMPLE 6

Drug Monitoring Machine

The signal interpretation engine is used to determine the presence and type of drugs in the body by means of an analysis of the brainwaves and bodywaves of an individual.

Step 1. Sensors are used or drug intake is monitored to assess and measure the type, timing, and level of drug(s) present in the body.

Step 2. Brainwaves and various other bodywaves are labeled by drug type, level, and time-course in the body.

Step 3. The drug-labeled wave segments (epochs) are used in the learning system to produce personalized drug interpretation maps which will be tuned to an individual's physiological reaction to the particular drug type.

Step 4. The drug interpretation maps are used with the classification system to diagnose the type and presence of drugs in the body.

Step 5. The drug-state classifications are used in pharmaceutical, toxicological, and other drug monitoring applications.

Step 6. The learning system is used to make new drug interpretation maps as needed to improve accuracy of drug-state classifications and to adjust to the particular drug monitoring application desired.

EXAMPLE 7

Personal Identification Machine

The signal interpretation engine is used to determine the identity of an individual, group, or organism; or to determine the type of structure or state present in a complex system. For individual identification from brainwave analysis, the following types of steps are taken.

Step 1. Sensors are used to measure the brainwaves of many individuals while they perform various cognitive tasks and other tasks involving the activation of various distinct neural circuits in the brain. In general each individual will accomplish the cognitive tasks using neural circuits that are configured at least slightly differently. The spatial and temporal structure of the resultant brainwave activities will therefore be at least slightly different. Discrimination of these differences is one of many tasks for which the signal interpretation engine is particularly well suited.

Step 2. The data binding and labeling module is used to select, define, label, and group brainwave segments (epochs) according to the individual who generated the brainwave epochs (individual-labeled brainwave epochs). Also the brainwaves are labeled by cognitive task (and temporal location during each cognitive task) for each individual. This will create a set of brainwave epochs labeled by both individual and cognitive state.

Step 3. The individual and cognitive state labeled brainwave epochs are used as inputs to the learning system to produce individualized cognitive state interpretation maps which will be tuned to an individual's particular cognitive states.

Step 4. The individualized cognitive state interpretation maps are used with the classification system to produce sequences of cognitive state classifications. These cognitive state classification sequences should match the true cognitive state sequences naturally engaged by the particular cognitive tasks used.

Step 5. The classified cognitive state sequences are compared with the true cognitive state sequences to determine which individual's brainwave epochs are being classified. The classification system may use individual-specific interpretation maps from each of many individuals. The individual interpretation maps corresponding to the most accurate cognitive state classification sequence will correspond to the particular individual whose brain generated the brainwave epochs currently being classified.

Step 6. Steps 1–3 are repeated to create increasingly accurate individual-specific cognitive state interpretation maps. Steps 4–5 are repeated to compare the true sequences with the classified cognitive state sequences obtained by using each individual's interpretation maps. In this way an individual may be identified from a group on the basis of an analysis of his brainwaves using the signal interpretation engine. Adjustments are made as needed to suit particular individual identification objectives.

EXAMPLE 8

Prosthetic Limb Animation Machine

The signal interpretation engine is used to accurately animate prosthetic or artificial limbs by using either brainwaves, muscle signals, neural signals in the stump, or some combination of these. These complex neural and muscle waves are generated by intentional volition to move the limb. The key is to interpret the intentional patterns present in these waves and use these interpretations to drive control mechanisms to animate the limb(s).

Step 1. Sensors are used to measure the signals and waves corresponding to neural and muscle activity on the head, stump(s), and other parts on the body.

Step 2. These muscle bodywaves and neural brainwaves are labeled by motor intention. This can be done by recording intention events while the patient plays various video games in which he is stimulated to imagine and mentally-intend the movement of his missing limb. This will produce motor intention labeled brainwave and bodywave segments (epochs).

Step 3. The motor intention labeled brainwaves and bodywaves are used in the learning system to produce personalized motor intention interpretation maps which will be tuned to an individual's neural and muscle response to mental intention to move his missing limb.

Step 4. The motor intention interpretation maps are used with the classification system to generate motor interpretations and control signals to drive and animate the artificial limb device. As a preliminary training step, the classification system can be used to first animate virtual objects and limbs in a computer software video game environment. After the patient has gained proficiency at animating virtual limbs, he can move on to actually animating his own physical prosthetic limbs.

Step 5. The learning system is continually used to make ever better motor intention interpretation maps to animate new additional degrees of freedom and to improve existing maps. In this way a patient can learn to first animate a single degree of freedom such as move his artificial thumb and later add additional degrees of freedom (additional interpretation maps) to animate his fingers, wrist, and additional complex and subtle motions of the hand. By continually making new interpretation maps, the maps will be able to follow the changes in the patient's nervous system which are sure to follow as he or she develops increasing control over his or her artificial limb.

EXAMPLE 9

Sleep-Stage Interpretation Machine

The signal interpretation engine is used to determine the sleep stage or state of sleep that an individual is currently experiencing from an analysis of his or her brainwaves and bodywaves. It can also be used to investigate the relationship between different stages of sleep. The signal interpretation engine can also be used to study the nature of differences between the sleep of different individuals.

Step 1. Sensors can be used to measure brainwaves and bodywaves of a sleeping patient.

Step 2. An expert human sleep stager can label brainwave and bodywave segments according to the stage and state of sleep he or she believes the brainwaves/bodywaves to represent.

Step 3. The sleep-stage labeled brainwave and bodywave segments are used in the learning system to produce personalized sleep-stage interpretation maps which will be tuned to an individual's physiological expression of his or her various sleep states.

Step 4. The sleep-stage interpretation maps are used with the classification system to classify new brainwave and bodywave epochs (new epochs which the learning system has never learned from) into the various stages of sleep. Best results are obtained when a patient's sleep stages are classified by using his or her own maps. However, useful differences between patients can create studies by using cross maps between patients and by studying the actual sleep-stage maps themselves.

Step 5. The learning system can be used to make new sleep-stage interpretation maps as needed to improve the accuracy of sleep-stage classifications and to adjust to the particular sleep-stage monitoring and classification application desired.

EXAMPLE 10

Sonar, Radar and other Signal Imaging Machines

The signal interpretation engine is used to identify and determine the class of objects at a distance (or nearby) by means of an analysis of the emitted and reflected waves coming from such objects. The signal interpretation engine identifies wave differences between signals coming from two objects that differ only slightly. The signal interpretation engine makes useful distinctions even in the presence of complex and noisy environments. The following steps should be followed to create and operate signal imaging machines using the signal interpretation engine.

Step 1. Sensors are used to measure the wave signals that are emitted from, transmitted through, and/or reflected from various objects of interest.

Step 2. The measured wave signals are labeled by the type, class, condition, or state of the object(s) from which the waves are coming.

Step 3. The type-labeled wave segments are used in the learning system to produce type interpretation maps which will be tuned to amplify differences between the different types, classes, conditions, or states of the objects under study.

Step 4. The type interpretation maps are used with the classification system to discriminate and classify new wave signals into object types.

Step 5. The learning system is used to make new type interpretation maps as needed to improve accuracy of the object-type classifications and to adjust to the particular type monitoring and classification application desired.

EXAMPLE 11

Weather Forecasting Machine

The signal interpretation engine is used to predict a certain feature or characteristic of the weather such as whether it will rain in San Francisco in two days or whether there will be high wind velocities next week in Oklahoma. In order to predict a particular weather feature, the following steps are taken:

Step 1. Weather historical data is used to create two prediction event lists for the two weather features that are to be predicted. The two prediction event lists are made by first deciding which weather feature is to be predicted, how far into the future it is to be predicted, and how much historical data is to be analyzed to make the prediction. For example, if we decide to try to predict whether it will rain in San Francisco in two days, we may consider the history of two hundred measured weather variables such as wind velocity, temperature, cloud coverage, and humidity from multiple sites in the vicinity of San Francisco and the Pacific Ocean off the coast of California during the previous two weeks, we create two prediction event lists as follows:

Step 2: The Rain list is a list of two week periods for which it rained in San Francisco (by some significant amount) two days into the future (from the end of the two week period of the data segment or epoch). The No-Rain list is a corresponding list for when it did not rain in San Francisco (by some significant amount) two days into the future.

Step 3. The two prediction event lists (Rain and No-Rain) are used with the labeler to cut out and shape those two week wave segments from the multiple time series of the two hundred selected weather variables (In general, the higher the sampling rate of these weather variables the better for prediction purposes).

Step 4. The Rain segments and the No-Rain Segments (as separate and distinct prediction-event examples) are fed into the map creator (learning algorithm) to create an intelligent rain prediction interpretation map designed and tuned to discriminate between Rain and No-Rain (in San Francisco two days into the future) from segments of time series data from two hundred measured weather variables.

Step 5. The efficacy and value of the constructed rain prediction map is tested by using the classification system (classifier) with the rain prediction map to classify other historical weather data (wave segments cut and shaped by the parser) which the learning algorithm has never before seen. If the classifier (using the rain prediction map) can accurately predict a significant fraction of the Rain and No-Rain events then the prediction map is likely to be useful and valuable as a two day San Francisco rain predictor. The more market weather measures considered, and the more wave segment examples presented to the learning algorithm, the better are the chances of constructing a rain prediction map that is truly useful and valuable for prediction purposes. The more test data (wave segments) that are classified for testing purposes the better the chances of understanding correctly the true value, capability, accuracy, and potential of the constructed rain prediction map.

Step 6. The rain prediction map is used with the classifier to predict Rain or No-Rain (and thus to classify into the two day future Rain and No-Rain states in San Francisco) from new segments prepared by the parser from the multiple time series of multiple weather market measures. In this way the map can be used as a weather predictor.

Step 7. Periodically new prediction maps are constructed to improve accuracy and follow possibly changing predictive patterns within the multiple weather measure time series.

Step 8. Other different maps are constructed to predicted different features of the weather both locally and globally and for different periods into the future (other than two days), using different collections of weather measures (other than the two-hundred measures used in the above example), and by analyzing wave segments of different lengths (other than two weeks). Maps to predict features of other weather events (other than San Francisco Rain) and of different weather types (such as wind levels and temperatures) are then constructed.

Step 9. The different constructed prediction maps are carefully tested and evaluated to decide which are the most predictive, accurate, and reliable.

Step 10. The weights in the prediction maps are analyzed to see which features of which weather measures are the most important for particular predictive purposes and thereby gain additional useful understanding of weather patterns and weather mechanisms. This understanding is used to further improve the accuracy of future maps that are constructed.

EXAMPLE 12

Determination of Relationships between Event Types

The signal interpretation engine is used to explore, investigate, and determine the relationship between different types of events by means of an analysis of the classification reliability table produced by the classification module within the map generation module. To determine the relationship between two or more distinct sets of event types the following steps are taken.

Step 1. Sensors are used to measure the event types and corresponding signal data.

Step 2. Signal data is labeled into segments by event type.

Step 3. The event type is used to labeled wave segments in the learning system to produce event type interpretation maps which will be tuned to the differences in signal data between two or more event types.

Step 4. New labeled data and the event type interpretation maps are used with the classification system to verify that the interpretation maps are accurate to a desired degree of accuracy by comparing the true event types with the classified event types.

Step 5. After interpretation maps of high accuracy are obtained, the structure of the reliability tables is studied for the optimal consolidators corresponding to the event type interpretation maps. These reliability tables contain useful information concerning the relationship between different event types. If the reliability tables are nearly diagonal then the event type sets are nearly disjoint or exclusive. Large off-diagonal elements in the tables indicates overlapping event type sets. Additional information concerning the event type sets under study can be gathered from structural analysis of the reliability tables.

EXAMPLE 13

Scientific Signal and Wave Analysis Tools

The signal interpretation engine is used in scientific research software tools for signal display, analysis, and interpretation. It is used in software tools that integrate the elements of signal and wave display on a computer screen, and that label signal segments by event type, generate of interpretation maps, and segment classification into event types by using the interpretation maps.

Subsets of the following software components or elements are made available to the user in an integrated software display and interpretation executable to facilitate research on wave signals or other signal data and to allow the user to quickly discover new methods for interpreting the data by using the signal interpretation engine: raw signal, wave, and time series data coming from a digitization of the raw measurement data obtained from sensors or measurement devices; event type indicators to indicate types, states, conditions, modes, and states corresponding to the signal data; binding between event type and signal data; feature maps and feature segments; weight tables; superposition segments; aggregator operators; attribute values; event-type activations, event-type probabilities, event-type memberships, event-type confidence levels, event-type classifications, visual icons corresponding to event-type classifications, epoch feature segments, weight-tables, aggregators, distribution functions, and typing-confidence functions.

EXAMPLE 14

Software Tools for the Development of Device Drivers

The signal interpretation engine is used in software development tools to create and develop device drivers to control computer games, computer software, and virtual and real devices. The components of these integrated driver development software executables are subsets of the following: display software to display signals; events, interpretations, and the status of virtual and real devices controlled by streams of continuous interpretations coming from the classifier in real time mode; off-line animators to simulate the stream of interpretations and control signals and animate the devices and software animated by such control streams; real-time animators to develop real-time driver applications in which speed is a critical factor; games controlled and animated by streams of interpretations and control signals generated by the classification system in conjunction with a previously-made interpretation map; hardware to deliver control signals to mouse, keyboard, joystick, and other input ports to allow the classification system to deliver real-time control signals "under" the operating system to allow the control signals to work with virtually any existing software including software which was not specifically designed to work with the signal interpretation engine.

EXAMPLE 15

Integrated Background MindState Interpretation and Mind-Mouse Control Applications that are Virtually Transparent to the Computer User The signal interpretation engine is used in software and hardware applications in which the classification system and/or the learning system are used in a real-time (fast, rapid, speedy) mode in such as way as to be mostly or completely unnoticed and virtually transparent to the computer user. This is accomplished by having the signal data and event type data measured and recorded in an automatic fashion without the need for user intervention, and by having the data binding, generation of interpretation maps, classification, and generation and delivery of the control signals accomplished with executables which run in the background and interact with user software by means of shared memory, or other communication means between or within executables.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus for providing an interpretation corresponding to a signal, the apparatus comprising a computer programmed to run a plurality of modules comprising:

a feature expansion module containing feature operators operating on a signal, expanding the signal to form a plurality of feature segments, each feature segment corresponding to a unique representation of the signal across an epoch corresponding to an event occurring within a time segment, the event having a type;

a consolidation module for forming inner products between the plurality of feature segments and a weight table comprising weight elements, and for applying aggregators to consolidate the inner products into a distribution function representing an attribute over a domain, the domain having one or more values;

a map generation module for producing an interpretation map reflecting a preferred weight table and aggregator to be applied to the signal data to characterize the event.

2. The apparatus of claim 1, wherein the domain reflects a selected weight table, aggregator, and event type, corresponding to each value of the attribute.

3. The apparatus of claim 1, further comprising a data module for processing the signal data; and a control module for controlling execution of the modules.

4. The apparatus of claim 3, wherein the control module is further programmed to provide selections to a user for controlling creation and use of the weight table, aggregators, and feature operators.

5. The apparatus of claim 3, wherein the data module is further programmed to process the signal data for creating signal segments, each signal segment corresponding to an epoch, and bound to an event type corresponding to the event.

6. The apparatus of claim 1, wherein the feature expansion module is further programmed to characterize the signal data in terms of a plurality of variables, creating a feature map relating each feature segment to a feature operator creating the feature segment, and selected values of the plurality of variables corresponding to the feature operator and the feature segment.

7. The apparatus of claim 1, further comprising a weight table module for providing a weight table comprising weight elements having a weight corresponding to at least one feature segment of the plurality of feature segments.

8. The apparatus of claim 7, wherein the weight table module is further programmed to receive an input for selecting the weight table.

9. The apparatus of claim 1, wherein the weight elements of the weight table are formed from the feature segments.

10. The apparatus of claim 1, wherein the weight elements of the weight table correspond to variables used by the feature operators to create the feature segments.

11. The apparatus of claim 10, wherein the weight table further comprises a number of elements corresponding to the number of feature segments.

12. The apparatus of claim 1, wherein the consolidation module further comprises a superposition module, an aggregation module, and an ordering module.

13. The apparatus of claim 12, wherein the superposition module is programmed to superimpose a plurality of feature segments into a single superposition segment.

14. The apparatus of claim 12, wherein the aggregation module is further programmed to aggregate a plurality of superposition segments provided by the superposition module into a plurality of attribute values, and wherein the ordering module is further programmed to order the attribute values into a plurality of distribution functions relating the attribute values to an event type, an instance of an event, a weight table selected, and an aggregator operator selected for use by the aggregator module of the consolidation module.

15. The apparatus of claim 12, wherein the aggregation module is further programmed to aggregate a plurality of superposition segments provided by the superposition module into a plurality of attribute values, and wherein the ordering module is further programmed to order the attribute values into a plurality of distribution functions relating the attribute values to an event type, an instance of an event, a weight table selected, and an aggregator operator selected for use by the aggregator module of the consolidation module.

16. The apparatus of claim 1, wherein the map generation module further comprises a typing confidence module for applying typing confidence operators to distribution functions to provide a typing confidence function.

17. The apparatus of claim 16, wherein the map generation module further comprises a classification module programmed to receive attribute threshold values from the typing confidence module, and to use the attribute threshold values to classify the epoch according to an event type corresponding to the event of the epoch.

18. The apparatus of claim 17, wherein the classification module is further programmed to provide a measure of classification reliability for the event type selected to correspond to the event.

19. The apparatus of claim 18, wherein the measure of classification reliability comprises a reliability table for indicating a degree to which a classified event type accords with a true event type.

20. The apparatus of claim 19, wherein the reliability table comprises a relationship between two or more event types.

21. The apparatus of claim 1, wherein the consolidation module further comprises an optimization module for providing the interpretation map.

22. The apparatus of claim 21, wherein the optimization module is further programmed to use a discrimination expression in association with discrimination criteria to determine a satisfaction value corresponding to a consolidator comprising a weight table and an aggregator in combination.

23. The apparatus of claim 22, wherein the optimization module is further programmed to provide in the interpretation map a plurality of parameters for identifying signal processing, feature expansion, consolidation, and classification of the event.

24. The apparatus of claim 23, wherein classification of the event comprises classification of epoch data into a pair of event types.

25. The apparatus of claim 23, wherein the interpretation map further comprises integration data for identifying methods of integrating at least two interpretation maps into an integrated interpretation map.

26. The apparatus of claim 1, wherein the signal data is selected from the group consisting of data from a medical context, a research context, and an industrial context.

27. The apparatus of claim 26, wherein the signal data is from a medical context, and the medical context is selected from the group consisting of a disease, a physical impairment, a mental impairment, a medical procedure, and a therapy or treatment.

28. The apparatus of claim 27, wherein the medical context is a disease and the disease is selected from the group consisting of cancer, autoimmunity, a disease related to a cardiovascular condition, a viral infection, a neurological disease, a degenerative disease, a disease correlated with aging, and a disease correlated with stress.

29. The apparatus of claim 26, wherein the signal data is from a research context and the research context is selected from the group consisting of single-trial analysis, cognitive study, psychology, neurology, cardiology, oncology, study of sleep, study of breathing, study of body conductance, study of body temperature, plant study, insect study, animal study, pharmaceutical drug-effect study, population study, flow study, physical environment study, geology, seismology, astronomy, medical clinical research, molecular biology, neuroscience, chemistry, and physics.

30. The apparatus of 26, wherein the signal data is from an industrial context and the industrial context is selected from the group consisting of individual identification for security purposes, drug evaluation and testing, lie detection, vehicle vibration analysis, temperature diagnostics, fluid diagnostics, mechanical system diagnostics, industrial plant diagnostics, radio communications, microwave technology, turbulent flow diagnostics, sonar imaging, radar imaging, audio mechanism, yield optimization, efficiency optimization, natural resource exploration, information exchange optimization, traffic monitoring, spatial interpretation, and toxicology.

31. The apparatus of claim 1, wherein the interpretation map provides a control mechanism based on an event or series of events selected from the group consisting of rehabilitation, biofeedback, real-time and hands-free control of virtual and real objects, mind mouse and thinking cap for controlling objects, neural controlled devices and video games, muscle controlled devices and video games, conductivity controlled video games using skin conductance, hands-free voice-free computer assisted telepathy, communication for the deaf, mute, blind or severely disabled, and a mechanism aiding prosthetic use and control.

32. The apparatus of claim 1, wherein the interpretation map generates a prediction based on an event or series of events comprising an area of observation and monitoring selected from the group consisting of meteorology, a stock market, geology, astronomy, seismology, genetics, neurology, cardiology, and oncology.

33. The apparatus of claim 1, further comprising a computer display, the computer display comprising a display element selected from the group consisting of a raw epoch signal segment, a superposition segment, an event type activation, an event type probability, an event type membership, an event type confidence level, an even type classification, a visual icon corresponding to an event type classification, an epoch feature segment, a weight table, an aggregator, a distribution function, and a typing confidence function.

34. A method for providing an interpretation map, the method comprising:
providing signal data corresponding to an event, the event having a type;
expanding the signal data by applying a feature operator to create feature segments;
consolidating the feature segments by forming inner products between the plurality of feature segments and a weight table;
generating an interpretation map reflecting parameters for optimizing the feature expansion, consolidation, and classification of signal data into event types.

35. The method of claim 34, wherein consolidating the feature segments further comprises applying aggregators to consolidate the inner products into a distribution function representing an attribute over a domain, the attribute having one or more values.

36. The method of claim 35, wherein the domain comprises a domain reflecting a selected weight table, aggregator, and event type corresponding to each value of the attribute.

37. The method of claim 35, wherein consolidating further comprises superimposing a plurality of feature segments to provide a superposition segment and operating on a plurality of superposition segments to provide a distribution function.

38. The method of claim 37, further comprising applying a plurality of aggregator operators to a plurality of superposition segments, each superposition segment corresponding to a weight table, to provide a plurality of attribute values, each attribute value corresponding to a weight table and an aggregator operator.

39. The method of claim 38, further comprising ordering the attribute values in a distribution function relating each attribute value to an event type, an event instance, a weight table, and an aggregator operator.

40. The method of claim 35, wherein generating a map further comprises providing a typing confidence function using the distribution function and a typing confidence operator to relate a confidence value to a pair of event types and the attribute value.

41. The method of claim 34 further comprising controlling the method by providing selections from a user to control providing weight tables and aggregators.

42. The method of claim 34, further comprising providing a data module for processing the signal data to create epochs corresponding to time segments and bound to event types corresponding to the events.

43. The method of claim 42, wherein the event is selected from the group consisting of a keyboard, a mouse movement, a mouse button press, a touch-pad activity, a light-pen activity, a pointer activity, a joystick movement, a joystick button press, a software event, condition or state, a game event, condition or state, a presence of elements on a computer screen, a movement of elements on a computer screen, a sound from a speaker, a microphone reception of sound, an eye focus location, an eye movement, and a body or body-part movement.

44. The method of claim 42, wherein the interpretation map that is generated comprises an ability to provide a control mechanism for an event or series of events comprising a function selected from the group consisting of controlling the position and movement of a cursor on the screen, moving a game paddle, influencing the outcome of a game, modifying the operation of computer software, tracking the movement of attention, and monitoring comprehension.

45. The method of claim 34, wherein expanding further comprises providing feature operators corresponding to one or more variables to create a feature map reflecting the feature segments corresponding to the one or more variables and the feature operators for the signal data within an epoch.

46. The method of claim 34, wherein the weight table comprises weight elements having weights that are generated by processing feature segments, wherein the processing comprises adjusting the relative influence of each of the feature segments with respect to one another.

47. The method of claim 46, wherein each weight element corresponds to a selected feature segment and feature operator, corresponding to an ordered set comprising the variables corresponding to the feature segment.

48. The method of claim 34, further comprising providing a computer display, the computer display comprising a display element selected from the group consisting of a raw epoch signal segment, a superposition segment, an event type activation, an event type probability, an event type membership, an event type confidence level, an even type classification, a visual icon corresponding to an event type classification, an epoch feature segment, a weight table, an aggregator, a distribution function, and a typing confidence function.

49. The method of claim 48, wherein the interpretation map that is generated comprises an ability to develop an interpretation of an event or series of events.

50. The method of claim 48, wherein the interpretation map that is generated comprises an ability to provide a control mechanism for an event or series of events.

51. The method of claim 50, wherein the control mechanism comprises a simulated device driver or a real-time device driver.

52. The method of claim 48, wherein the interpretation map that is generated comprises an ability to generate a prediction based on an event or series of events.

53. The method of claim 34, wherein the method is applied to a task selected from the group consisting of developing an interpretation of an event or series of events, providing a control mechanism for an event or series of events, and generating a prediction based on an event or series of events.

54. The method of claim 53, wherein the task comprises developing an interpretation of an event or series of events comprising information selected from the group consisting of a medical context, a research context, and an industrial context.

55. The method of claim 54, wherein the information is from a medical context and the medical context comprises a condition selected from the group consisting of a disease, a physical impairment, a mental impairment, a medical procedure, and a therapy or treatment.

56. The method of claim 55, wherein the condition comprises a disease and the disease is selected from the group consisting of cancer, autoimmunity, a disease related to a cardiovascular condition, a viral infection, a neurological disease, a degenerative disease, a disease correlated with aging, and a disease correlated with stress.

57. The method of claim 54, wherein the information is from a research context and the research context is selected from the group consisting of single-trial analysis, cognitive study, psychology, neurology, cardiology oncology, study of sleep, study of breathing, study of body conductance, study of body temperature, plant study, insect study, animal study, pharmaceutical drug-effect study, population study, flow study, physical environment study, geology, seismology, astronomy, medical clinical research, molecular biology, neuroscience, chemistry, and physics.

58. The method of claim 54, wherein information is from an industrial context and the industrial context is selected from the group consisting of individual identification for security purposes, drug evaluation and testing, lie detection, vehicle vibration analysis, temperature diagnostics, fluid diagnostics, mechanical system diagnostics, industrial plant diagnostics, radio communications, microwave technology, turbulent flow diagnostics, sonar imaging, radar imaging, audio mechanism, yield optimization, efficiency optimization, natural resource exploration, information exchange optimization, traffic monitoring, spatial interpretation, and toxicology.

59. The method of claim 53, wherein the task comprises providing a control mechanism for an event or series of events and the control mechanism is selected from the group consisting of rehabilitation, biofeedback, real-time and hands-free control of virtual and real objects, mind mouse and thinking cap for controlling objects, neural controlled devices and video games, muscle controlled devices and video games, conductivity controlled video games using skin conductance, hands-free voice-free computer assisted telepathy, communication for the deaf, mute, blind or severely disabled, and a mechanism aiding prosthetic use and control.

60. The method of claim 53 wherein the task comprises generating a prediction based on an event or series of events comprising an area of observation and monitoring selected from the group consisting of meteorology, a stock market, geology, astronomy, seismology, genetics, neurology, cardiology, and oncology.

\* \* \* \* \*